US008267943B2

(12) United States Patent
Ferree

(10) Patent No.: US 8,267,943 B2
(45) Date of Patent: *Sep. 18, 2012

(54) METHODS AND DEVICES FOR BONE, JOINT, AND LIGAMENT RECONSTRUCTION WITH BANDS

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 747 days.

This patent is subject to a terminal disclaimer.

(21) Appl. No.: 12/030,081

(22) Filed: Feb. 12, 2008

(65) Prior Publication Data

US 2008/0195119 A1    Aug. 14, 2008

Related U.S. Application Data

(60) Provisional application No. 60/901,230, filed on Feb. 13, 2007.

(51) Int. Cl.
*A61B 17/70* (2006.01)
*A61B 17/04* (2006.01)

(52) U.S. Cl. ......... 606/139; 606/228; 606/232; 606/279

(58) Field of Classification Search .......... 606/246–264, 606/279, 139, 228, 232
See application file for complete search history.

(56) References Cited

U.S. PATENT DOCUMENTS

| 3,997,138 A | 12/1976 | Crock et al. |
| 4,146,022 A | 3/1979 | Johnson et al. |
| 4,854,304 A | 8/1989 | Zielke |
| 4,966,600 A | 10/1990 | Songer et al. |
| 5,092,867 A | 3/1992 | Harms et al. |
| 5,108,397 A | 4/1992 | White |
| 5,342,361 A | 8/1994 | Yuan et al. |
| 5,352,224 A | 10/1994 | Westermann |
| 5,387,213 A | 2/1995 | Breard et al. |
| 5,423,820 A | 6/1995 | Miller et al. |
| 5,496,318 A | 3/1996 | Howland et al. |
| 5,611,801 A | 3/1997 | Songer |
| 5,702,399 A | 12/1997 | Kilpela et al. |
| 5,704,936 A | 1/1998 | Mazel |
| 5,725,582 A * | 3/1998 | Bevan et al. .................. 606/263 |
| 5,782,831 A | 7/1998 | Sherman et al. |
| 5,904,682 A | 5/1999 | Rogozinski |
| RE36,221 E | 6/1999 | Breard et al. |
| 5,964,769 A | 10/1999 | Wagner et al. |

(Continued)

*Primary Examiner* — Pedro Philogene
(74) *Attorney, Agent, or Firm* — Pandiscio & Pandiscio

(57) ABSTRACT

Spinal stabilization mechanisms act to prevent lateral bending, extension, and rotation across adjacent vertebrae. Methods for spinal stabilization includes placing one or more anchors at each vertebral level, positioning one or more sutures around each anchor at each level such that the each suture forms a loop or band around two adjacent anchors, applying tension to the ends of each suture to tighten the suture loop around the anchors and welding overlapping ends of each suture together to form suture bands connecting the anchors and thereby preventing lateral bending, extension, and rotation of the spinal segment. A suture banding tool may be used to place the sutures around the anchors in a looped configuration, apply tension to the suture ends to tighten the suture loop around the anchors and weld the ends of the suture to form a suture band connecting the anchors. The suture banding tool includes a suture welding tool having opposing jaws having a gap therebetween for receiving a portion of a suture and a heating element for welding the suture, a suture holding device releasably attached to the suture welding tool having at least one recess for holding a portion of a suture in a looped configuration, and one or more sutures.

11 Claims, 23 Drawing Sheets

U.S. PATENT DOCUMENTS

| Number | Date | Inventor | Ref |
|---|---|---|---|
| 5,989,256 A | 11/1999 | Kuslich et al. | |
| 5,993,448 A | 11/1999 | Remmler | |
| 5,997,542 A | 12/1999 | Burke | |
| 6,033,429 A | 3/2000 | Magovern | |
| 6,093,205 A | 7/2000 | McLeod et al. | |
| 6,248,106 B1 | 6/2001 | Ferree | |
| 6,287,308 B1 | 9/2001 | Betz et al. | |
| 6,296,643 B1 * | 10/2001 | Hopf et al. | 606/263 |
| 6,423,065 B2 | 7/2002 | Ferree | |
| 6,645,211 B2 | 11/2003 | Magana | |
| 6,878,167 B2 | 4/2005 | Ferree | |
| 7,090,675 B2 | 8/2006 | Songer | |
| 7,201,774 B2 | 4/2007 | Ferree | |
| 7,776,069 B2 | 8/2010 | Taylor | |
| 7,799,060 B2 * | 9/2010 | Lange et al. | 606/257 |
| 2001/0027319 A1 | 10/2001 | Ferree | |
| 2002/0120269 A1 | 8/2002 | Lange | |
| 2003/0195514 A1 | 10/2003 | Trieu et al. | |
| 2004/0039392 A1 | 2/2004 | Trieu | |
| 2004/0260287 A1 | 12/2004 | Ferree | |
| 2006/0084985 A1 | 4/2006 | Kim | |
| 2006/0089646 A1 | 4/2006 | Bonutti | |
| 2007/0005062 A1 | 1/2007 | Lange et al. | |
| 2007/0073293 A1 * | 3/2007 | Martz et al. | 606/61 |
| 2007/0168035 A1 | 7/2007 | Koske | |
| 2007/0239158 A1 | 10/2007 | Trieu et al. | |
| 2008/0125779 A1 | 5/2008 | Ferree | |
| 2008/0195151 A1 | 8/2008 | Ferree | |
| 2008/0262550 A1 | 10/2008 | Ferree | |
| 2010/0076492 A1 | 3/2010 | Warner et al. | |
| 2010/0152779 A1 | 6/2010 | Allard et al. | |
| 2010/0211108 A1 | 8/2010 | Lemole, Jr. | |

* cited by examiner

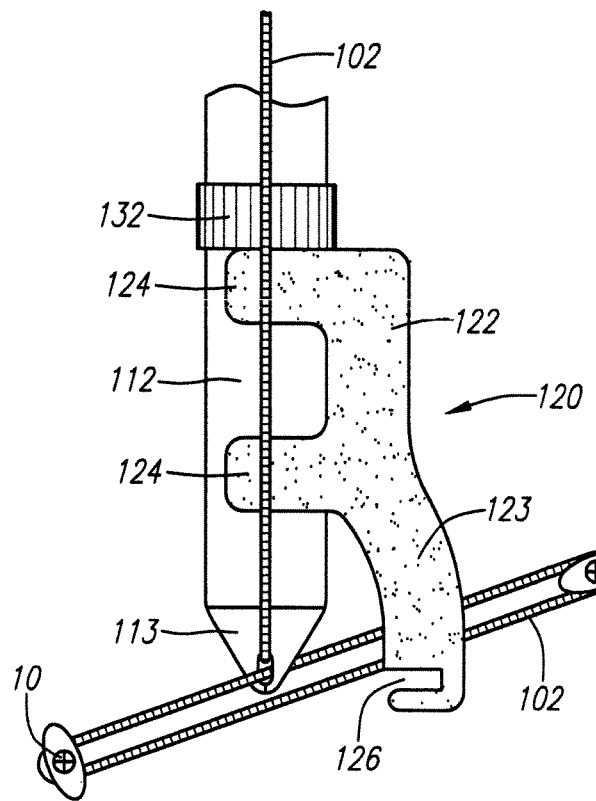
FIG. 5C
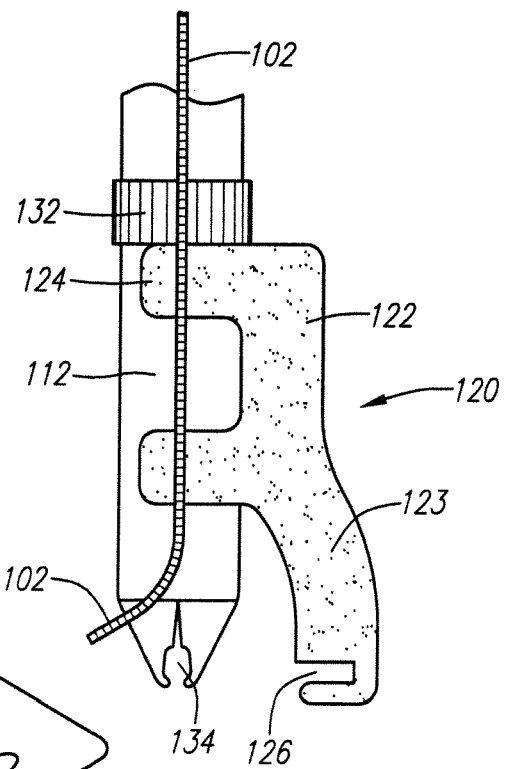
FIG. 5D
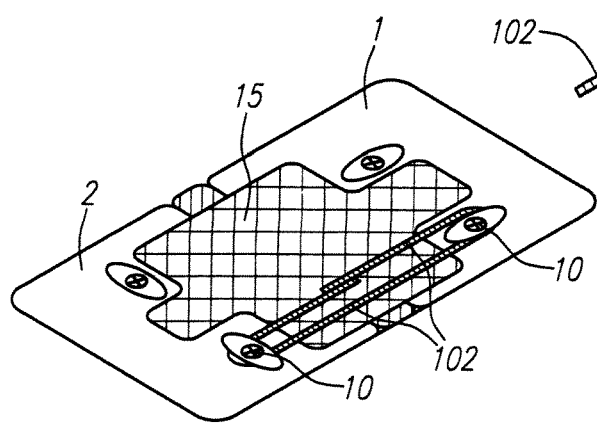

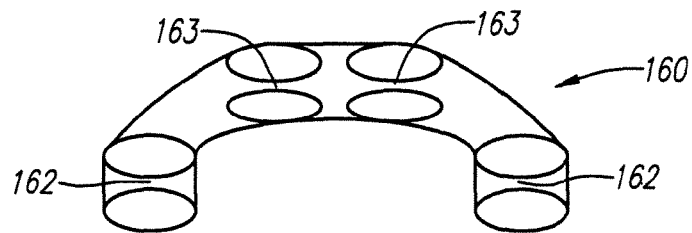
FIG. 9A
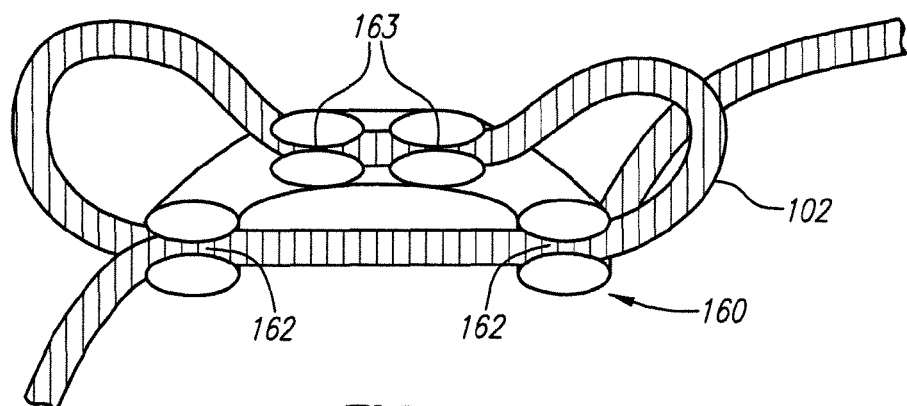
FIG. 9B
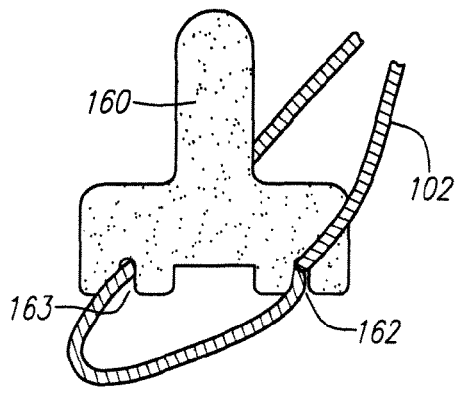 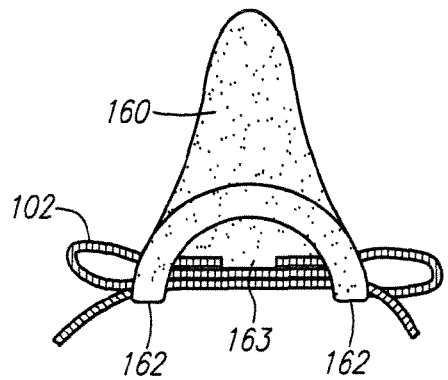
FIG. 9C  FIG. 9D

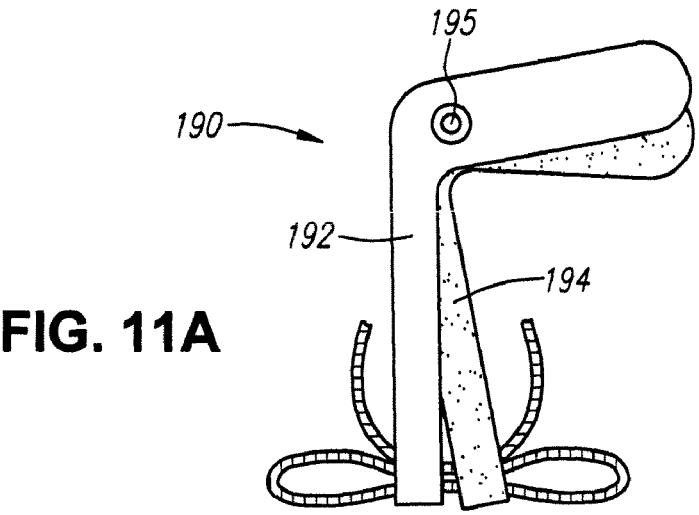
FIG. 11A
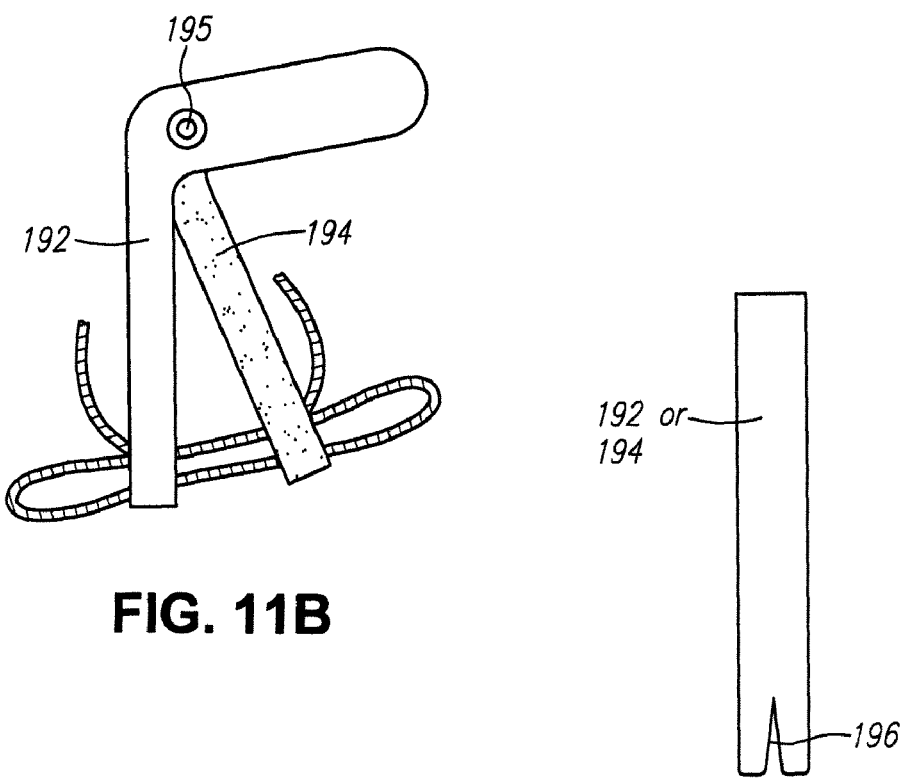
FIG. 11B
FIG. 11C

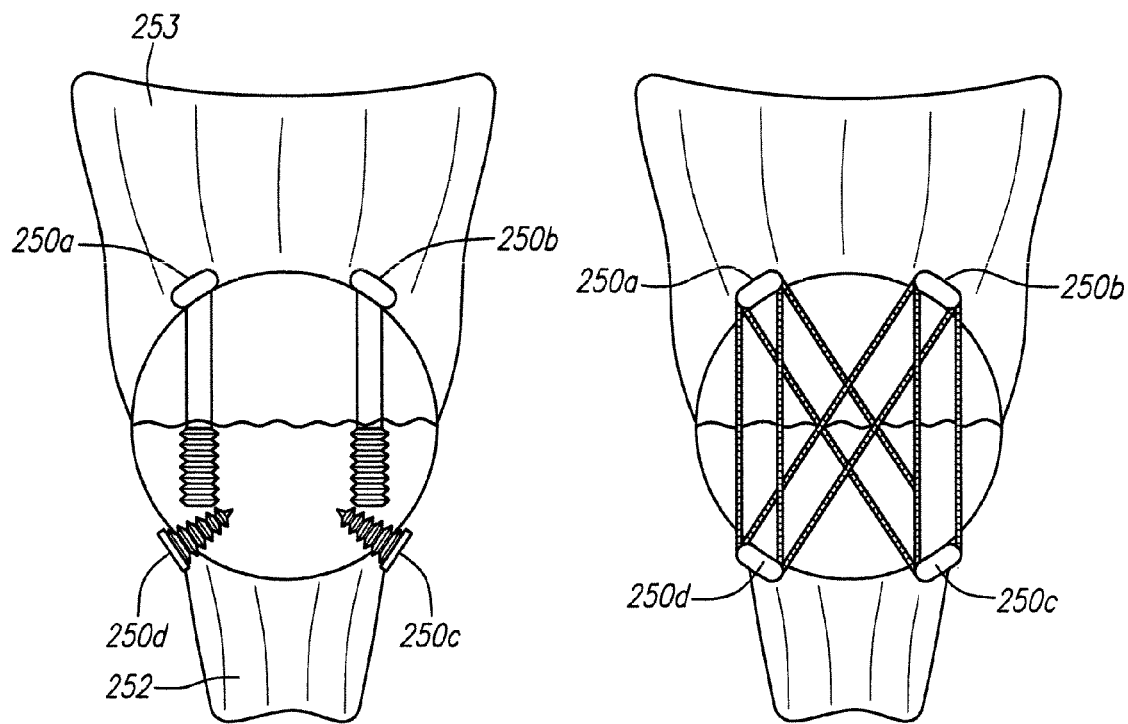
FIG. 13A  FIG. 13B
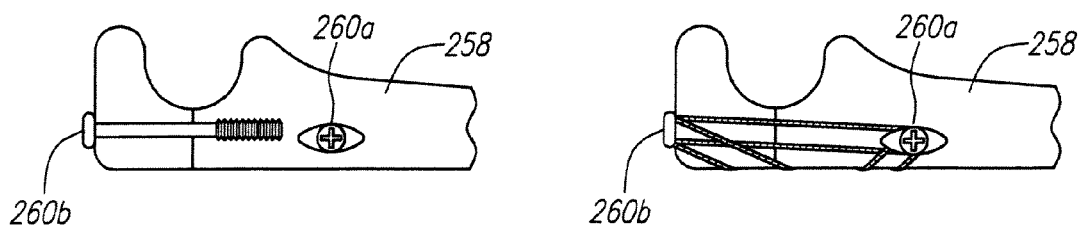
FIG. 14A  FIG. 14B

METHODS AND DEVICES FOR BONE, JOINT, AND LIGAMENT RECONSTRUCTION WITH BANDS

RELATED APPLICATIONS

This application claims the benefit of U.S. Provisional Application No. 60/901,230, filed Feb. 13, 2007, entitled "Bone, Joint and Ligament Reconstruction with Bands." This application is related to co-pending applications 60/808,795, filed May 26, 2006, entitled "Fastening Assemblies for Disc Herniation Repair and Methods of Use" and 60/861,499, filed Nov. 28, 2006, entitled "Anulus and Spinal Ligament Reconstruction." The application is also related to U.S. Pat. Nos. 6,248,106 and 6,423,065. All of the above-referenced patent and applications are hereby expressly incorporated by reference in their entirety.

FIELD OF THE INVENTION

The subject invention resides in methods and apparatus for reconstructing the annulus fibrosis (AF) of a spinal disc and the ligaments of the spine. The invention is particularly well suited to the prevention of extrusion of material or devices placed into the disc space and to the prevention of excessive spinal motion.

BACKGROUND

The human intervertebral disc is an oval to kidney bean-shaped structure of variable size depending on the location in the spine. The outer portion of the disc is known as the annulus fibrosis (AF). The annulus fibrosis is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The annulus fibrosis contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the annulus fibrosis. As discussed in co-pending U.S. patent application Ser. No. 10/407,554 and U.S. Pat. No. 6,878,167, the content of each being expressly incorporated herein by reference in their entirety, the posterior portion of the annulus fibrosis has abundant pain fibers.

Herniated nucleus pulposus (HNP) occurs from tears in the annulus fibrosis. The herniated nucleus pulposus often allies pressure on the nerves or spinal cord. Compressed nerves cause back and leg or arm pain. Although a patient's symptoms result primarily from pressure by the nucleus pulposus, the primary pathology lies in the annulus fibrosis.

Surgery for herniated nucleus pulposus, known as microlumbar discectomy (MLD), only addresses the nucleus pulposus. The opening in the annulus fibrosis is enlarged during surgery, further weakening the annulus fibrosis. Surgeons also remove generous amounts of the nucleus pulposus to reduce the risk of extruding additional pieces of nucleus pulposus through the defect in the annulus fibrosis. Although microlumbar discectomy decreases or eliminates a patient's leg or arm pain, the procedure damages weakened discs.

U.S. Pat. No. 6,248,106 is directed to spinal stabilization mechanisms operative to prevent lateral bending, extension, and rotation at the disc space. Broadly, the mechanism includes two or more anchors at each vertebral level, and links for each anchor at each level to both anchors at the other level, resulting in a cross-braced arrangement. In the preferred embodiment, the mechanism uses screws or anchors for placement in the vertebral bodies and cables, sutures or other elongate bands are used to connect the screws or anchors. The screws or anchors preferably include a post protruding from the vertebra, and cable holder which fits over the post. The cables or sutures can be threaded through the cable holders and pulled together to connect the anchors and apply compression across the disc space. The cables or sutures can be connected in various vertical, horizontal and/or diagonal arrangements across the anchors to provide the necessary resistance to lateral bending, extension, and/or rotation at the disc space. In addition, bone graft, cages, or distracting plugs and the device to enhance fusion area would fill or cross the disc space. The bone graft, cages, etc. within the disc space are preferably used to resist compression.

Based on the above, there is a need for a devices and methods for positioning one or more sutures across the two or more anchors at each vertebral level which is simple and safe to be installed during surgery and which allows an easy adjustment of the suture during surgery according to the actual clinical requirements.

SUMMARY

A portion of the annulus fibrosis and a portion of the ligaments of the spine are excised to allow insertion of materials and devices into the disc space. For example, a portion of the anterior half of the annulus fibrosis and a portion of the anterior longitudinal ligament (ALL) are excised to enable insertion of bone growth promoting materials and fusion devices in interbody fusion procedures. Removal of portions of the annulus fibrosis and anterior longitudinal ligament increase the flexibility of the spine and allow excessive motion of the spine. For example, removal of the tissues mentioned permits excessive spinal extension, lateral bending, and axial rotation. Destabilizing the spine decreases the chance of a successful fusion. The invention may be used to increase the stiffness of the operated segment of the spine.

A portion of the annulus fibrosis and a portion of the anterior longitudinal ligament are also excised to enable insertion of motion preserving devices into the disc. For example, Total Disc Replacements (TDRs) and Nucleus Replacements (NRs) are often inserted through the anterior portion of discs. Excessive spinal extension, lateral bending, and axial rotation following excision of the spinal tissues and insertion of motion preserving devices into the disc space places excessive force on the facets of the spine. Biomechanical studies show the forces across the facets at the operated level of the spine can be doubled by motion preserving devices and the techniques used to insert such devices. Excessive force on the facets may lead to degeneration of the facets. Degeneration of the facets may cause low back pain.

The present invention provides methods for spinal stabilization operative to prevent lateral bending, extension, and rotation across adjacent vertebrae. Broadly, the method includes placing one or more anchors at each vertebral level, positioning one or more sutures around each anchor at each level such that the one or more sutures form a loop or band around at two adjacent anchors, applying tension to the sutures to tightening the suture loop around the anchors and welding the suture band to connect the anchors thereby preventing lateral bending, extension, and rotation of the spinal segment. The invention may be used in the cervical, thoracic, lumbar or sacral regions of the spine.

In some embodiments, four anchors can be used to join two adjacent vertebrae. Two anchors are placed in each vertebra. The screws or anchors preferably include a post protruding from the vertebra and an enlarged head protruding from the post. A first suture in a looped configuration is placed over an anchor in the first vertebra and an anchor in the second vertebra. Tension is applied to the suture ends to tighten the loop around the posts of the anchors and the overlapping ends of the suture are then welded together to form a suture band connecting the anchors. A second suture in a looped configuration is placed over a second anchor in the first vertebra and an anchor in the second vertebra. Tension is applied to the suture ends to tighten the loop around the posts of the anchors and the overlapping ends of the second suture are then welded together to form a second suture band connecting the anchors. The first and second suture bands can be arranged in a pattern having any combination of diagonal connections, generally upper and lower horizontal connections, and/or generally left and right vertically extending connections to minimize or prevent extension, lateral bending, and rotation of the spinal segment. For example, the suture bands can be arranged in a diagonal pattern, a horizontal pattern, a vertical pattern or any combination thereof across the adjacent vertebrae. In some embodiments, further tension can be applied across the sutures band prior to welding to further tighten the band around the anchors and provide compression across the disc space between the adjacent vertebrae. In other embodiments, two or more suture bands may be placed around each anchor to provide additional tension and compression across the spinal segment.

In some embodiments a suture banding tool may be used to position one or more sutures around one or more anchors in two vertebrae. Once first and second anchors have been attached to first and second vertebrae, a suture banding tool comprising a welding tool, a holding device and at least one suture held in the holding device is advanced adjacent to the first and second anchors. A looped portion of the suture is placed around the shaft of the first and second anchor and tension is applied to the first and second ends of the suture to tighten the looped portion around the first and second anchors. The overlapping ends of the suture are welded together to form a suture band, or loop, connecting the first and second anchors. The suture ends are cut from the suture band and then the suture banding tool and suture ends are withdrawn.

In some embodiments, the suture banding tool may comprise a welding tool and a holding device. The welding tool may comprise an elongate member having a distal region, first and second opposing jaws with a gap therebetween configured to receive at least one suture and a heating element adapted to weld the at least one suture located in the distal region. The holding device may be releasably mounted on the welding tool. The holding device may comprise a second elongate member having a distal end that extends a fixed distance from the distal end of the welding tool and that has at least one recess adapted to receive a portion of at least one suture. In some embodiments, the holding device comprises an elongate tubular member having proximal and distal ends and a lumen extending therebetween. The proximal end is configured to releasably attach to the welding tool such that the welding tool is inserted in the lumen of the holding device. The distal end of the elongate tubular member further comprises one or more notches configured to hold at least a portion of one or more sutures in a looped configuration. In alternative embodiments, the holding device comprises an upper portion configured to releasably attach to the welding tool and a lower portion comprising an elongate arm extending at an angle from the longitudinal axis of the welding tool. One or more recesses configured to cooperate with the suture welding tool to hold a portion of at least one suture in a looped configuration is located in the distal end of the elongate arm.

The invention may also be used to treat other orthopedic conditions. For example, the invention may be used to treat fractures, such as fractures of the patella and olecranon. The invention may also be used to immobilize joints during fusion procedures. The invention may also be used with prosthetic joints.

BRIEF DESCRIPTION OF THE DRAWINGS

FIG. 5C is a lateral view of the embodiment in FIG. 5B showing the suture loops placed around two anchors.

FIG. 5D is an exploded view of the embodiment in FIG. 5C and an anterior view of a portion of the spine showing the suture welded into a band around the two anchors and released from the suture holding tool.

FIG. 9A is a view of the proximal end of an alternative suture loading tool.

FIG. 9B is a view of the proximal end of the embodiment in FIG. 9A with a suture loaded thereon.

FIG. 9C is a lateral view of the embodiment of FIG. 9B.

FIG. 9D is an anterior view of the embodiment of FIG. 9B.

FIG. 11A is a lateral view of an alternative suture holding device.

FIG. 11B is a lateral view of the embodiment of FIG. 11A showing the handle portions compressed.

FIG. 11C is end view of one of the elongate members of the suture holding tool of FIG. 11A.

FIG. 13A is an anterior view of coronal cross section of the patella with four anchors inserted around a transverse fracture illustrating an alternative embodiment of the invention.

FIG. 13B is an anterior view of the embodiment of 13A showing suture bands placed around the anchors.

FIG. 14A is a lateral view of a sagittal cross section through the ulna with anchors inserted around a fracture illustrating an alternative embodiment of the invention.

FIG. 14B is a lateral view of the proximal portion of the ulna and the embodiment of the invention drawn 14A showing a suture band placed around the anchors.

DETAILED DESCRIPTION

Devices in Various Spinal Segments

Figure 1A:
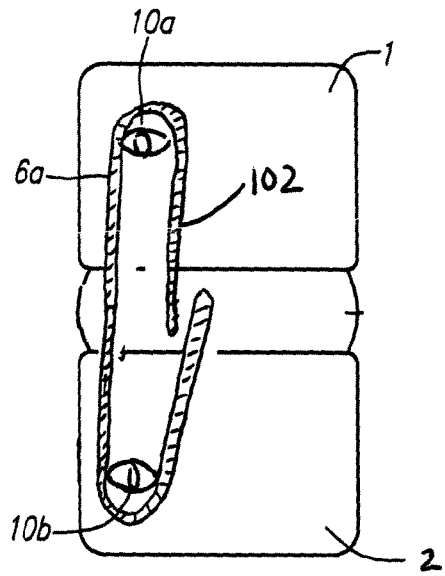
FIG. 1A is an anterior view of a segment of a spine with suture anchors placed in adjacent vertebrae and a suture loop placed around the anchors.
Figure 1B:
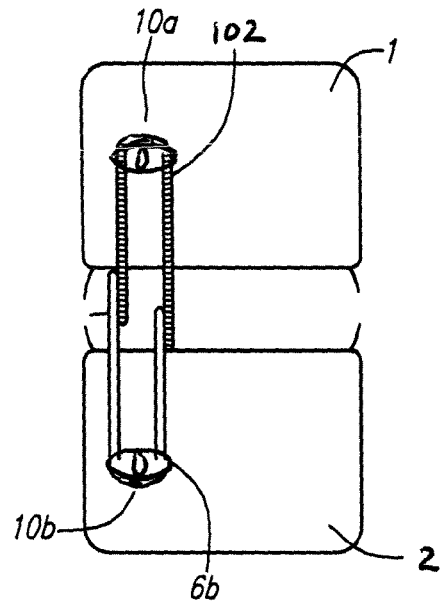
FIG. 1B is an anterior view the embodiment of FIG. 1A with the suture loop tightened around the anchors and welded to form a band connecting the anchors.

FIG. 1A-B illustrates a method using one or more suture bands to join adjacent vertebrae. Anchors 10a and 10b are placed in vertebrae 1 and 2 respectively. Each of anchors 10a, 10b has a post configured to be inserted in to the vertebra and an enlarged head or transverse component protruding from the end of the post. Suture 102 is placed around the posts of anchor 10a and anchor 10b in a loose "looped" configuration. The suture 102 is made of a material than can be welded together such as monofilament or multifilament configurations of nylon, polypropylene, polyester, polyethylene, or other suitable material. For example, in some embodiments, the suture can comprise a polyester suture, braided polyethylene or a metal cable.

As shown in FIG. 1B, the suture 102 is tightened around the posts of anchors 10a,b by pulling on first and second ends of the suture to reduce the size of the loop until opposing sides of the suture loop are held against the posts of the anchors 10a,b thereby connecting the anchors 10a,b and the vertebrae 1 and 2. Once the suture 102 has been sufficiently tightened around the anchors 10a,b overlapping ends of the suture 102 are welded together to form a suture band that connects anchors 10a,b. The enlarged head of each anchor 10a,b prevents the tightened suture loop from slipping off of the anchors 10a,b. The excess suture ends are then cut off at the weld and removed. In some embodiments, the suture loop may be further tightened to bring the anchors closer together and apply tension across the disc space. In alternative embodiments two or more suture bands may be placed around the suture anchors to apply additional tension across the disc space. In addition, the suture band material can be selected to be more or less flexible to provide the needed tension across the anchors.

Figure 2:
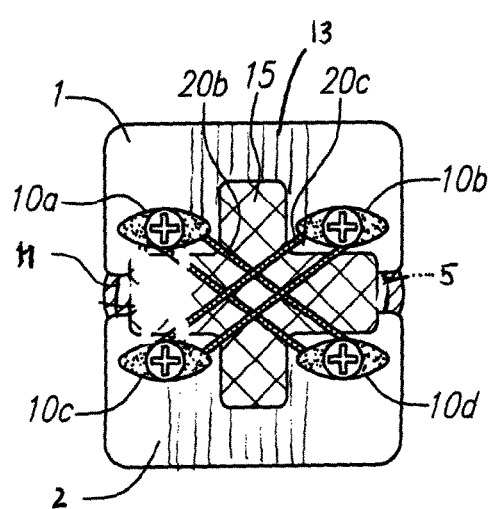
FIG. 2 illustrates an anterior view of a segment of a spine with two suture anchors placed in each adjacent vertebrae and suture bands connecting the anchors in a cross-braced arrangement

In some embodiments one or more suture bands may be used to hold a disc replacement device in place in disc space between adjacent vertebrae. In alternative embodiments, one or more suture bands can also be used to apply compression across adjacent vertebrae and minimize or prevent extension, lateral bending and/or rotation of the spinal segment. For example, as shown in FIG. 2, two suture bands may be used to stabilize a spinal segment after a portion of the annulus fibrosis and/or a portion of the ligaments of the spine have been excised during insertion of an intradiscal device. Here, an intradiscal device 5 is inserted between adjacent vertebrae 1,2. The anterior portion of the annulus fibrosis 11 and the anterior longitudinal ligament 13 are excised to permit insertion of the intradiscal device 5, such as a total disc replacement (TDR), a nucleus replacement (NR), or another intradiscal device, into the disc space. Two suture anchors 10a, 10b are placed into the vertebra 1 cranial to the disc and two suture anchors 10c, 10d are placed into the vertebra 3 caudal to the disc. The anchors 10a-d can vary in size from about 3 to about 12 mm in diameter and about 4 to about 40 mm in length. For example, anchors having a diameter of about 3 mm and a length of about 7 mm can be used in the anterior portions of cervical vertebrae. Additionally, anchors having a diameter of about 8 mm and a length of about 35 mm can be used in the anterior portions of lumber vertebrae. The anchors are preferably made of an MRI-compatible material. For example, the anchors can be made of titanium, plastic, or other material. The anchors can additionally be coated with a material, such as hydroxyappetite, that promotes the in-growth of bone.

The anchors 10a,b,c,d each have a post configured to be inserted into the vertebra and an enlarged head or a separate transverse elongate member connected at the head of the anchor for wrapping a suture band around the anchor. Examples of anchors suitable for use with the following methods are described in further detail in co-pending U.S. patent application Ser. No. 11/945,994, "entitled "Methods of Anterior Fixation and Stabilization of a Spinal Segment," filed on Nov. 27, 2007 and in co-pending U.S. patent application Ser. No. 12/030,109 entitled "Methods of Bone, Joint, and Ligament Reconstruction," filed on Feb. 12, 2008, both of which are incorporated by reference in their entirety herein.

Suture 102a is placed around the posts of anchor 10a in the right side of cranial vertebrae 1 and anchor 10d in the left side of caudal vertebrae 2 in a loose "looped" configuration. Suture 102b is placed around the posts of anchor 10b in the left side of cranial vertebrae 1 and anchor 10c in the right side of caudal vertebrae 2 in a loose "looped configuration. The sutures 102a,b are tightened around the posts of anchors 10a,d and 10b,c by pulling on first and second ends of each suture 102a,b to reduce the size of the suture loops until opposing sides of the suture loop are held against the posts of the anchors 10a,d and 10b,c connecting the anchors 10a,d and 10b,c and thereby connecting vertebrae 1 and 2. In some embodiments, the anchors 10a,b,c,d may be initially only partially inserted into the vertebrae 1,2 such that a larger portion of the post protrudes from the vertebrae 1,2 for engaging the suture loop. Once the sutures 102a,b have been looped over the anchors 10a,b,c,d the anchors may be fully advanced into the vertebrae 1,2. Further advancing the anchors 10a,b, c,d reduces the profile of the device. Advancement of diverging anchors could also be performed to increase tension on the suture bands 102a,b. The enlarged head of each anchor 10a, b,c,d prevent the sutures 102a,b from slipping off of the anchors 10a,b,c,d.

Once the sutures 102a,b have been tightened around the anchors 10a,d and 10b,c, the overlapping ends of each suture 102a,b are welded together to form suture bands connecting anchors 10a,d and 10b,c. The ends of the sutures 102a,b are cut just distal to the welded area of the suture bands to remove the excess suture material. In some embodiments, the suture loop may be further tightened prior to welding to bring the anchors 10a,d and 10b,c closer together and apply additional tension across the disc space between vertebrae 1,2. In addition, the arrangement of the suture bands across the anchors 10a,b,c,d, the number of suture bands placed across the anchors 10a,b,c,d and the tension applied to the sutures prior to welding can be varied depending on the intradiscal device used device used, whether the sutures are used to hold the disc replacement device in place or additionally to provide stabilization to the spine and the type of stabilization required. For example, as shown in FIG. 2, the sutures 102a,b can arranged in a cross-braced arrangement having two diagonal suture bands connecting anchors 10a,d and 10b,c. In an alternative embodiment, any number of sutures can be arranged to form one or more vertical suture bands, one or more diagonal suture bands and/or one or more horizontal suture bands for holding the device 5 in the interdiscal space and for stabilizing the portion of the spine where the annulus fibrosis 11 was excised in order to place the intradiscal device 5.

In some embodiments, as shown in FIG. 2, an in-growth component 15, such as a piece of porous mesh material, can be placed between the suture bands 102a,b and the vertebrae 1,2. The mesh 15 acts as scaffolding for connective tissue in-growth from the annulus fibrosis 11, the anterior longitudinal ligament 13, and the vertebrae 1,2 In addition, an anti-adhesion component can be placed over the in-growth component 15, anchors 10a-d, suture bands 102a,b and vertebrae 1,2 and 5. The anti-adhesion cover can be made of a material that discourages tissue in-growth or adhesions, such as ePTFE, Sepratfilm, allograft, or other absorbable materials, in order to prevent adhesions to the suture bands, in-growth component, and the anchors and to prevent injury to delicate structures such as nerves, blood vessels, and the esophagus that lie directly over the anchors.

Devices in Other Bones and Ligaments

One or more suture bands may also be used in conjunction with one or more anchors to join fractures or reconstruct bones or ligaments in other portions of the body. FIG. 13A is an anterior view of coronal cross section of the patella, the patella tendon 252 (distal to the patella), a portion of the quadriceps muscle 253, and an alternative embodiment of the invention. Two screws 250a-d have been inserted across a transverse fracture in the patella. Two screws have been placed into the distal pole of the patella. FIG. 13B is an anterior view of the patella, the patella tendon, a portion of the quadriceps muscle with four suture bands connecting the anchors 250a,b,c,d in a vertical and diagonal arrangement. The suture bands were applied over the screws in the manner described above.

FIG. 14A is a lateral view of a sagittal cross section through the proximal ulna 258 with anchors 260a and b disposed therethrough. FIG. 14B is a lateral view of the proximal portion of the ulna 258 and the embodiment of the invention drawn 14A. A suture band 202a has been placed around anchors 260a,b according to the method described above to connect anchors 260a,b and thereby join the fractured segments of the ulna 258.

Figure 14C:
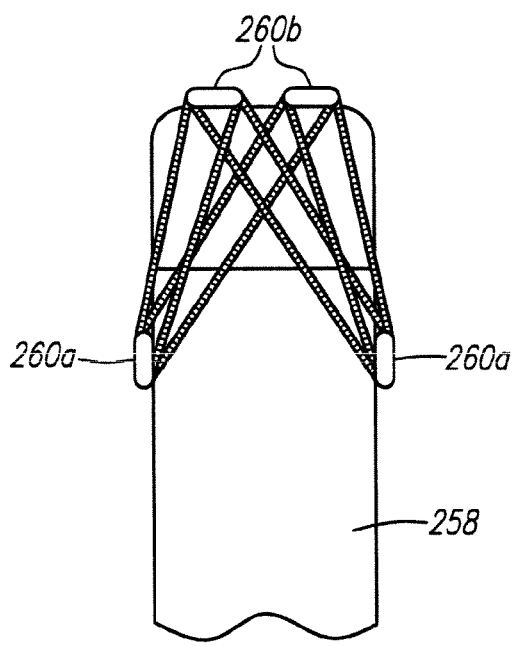
FIG. 14C is posterior view of a portion of the ulna and the embodiment of the invention drawn in FIG. 14B.

FIG. 14C is posterior view of a portion of the ulna and the embodiment of the invention drawn in FIG. 14B. Two screws 260b,d have been inserted across a fracture through the olecranon. Two screws 260a,c have also been inserted into the ulna 258 distal to the fracture. Additional suture bands 202b, c,d were applied over the screws in the manner taught previously to further hold the fractured segments together. The screws are preferably placed in different planes to minimize the stress risers from the holes in the bone. The invention may be used to treat fractures of the other bones of the axial skeleton or the extremities.

Figure 15A:
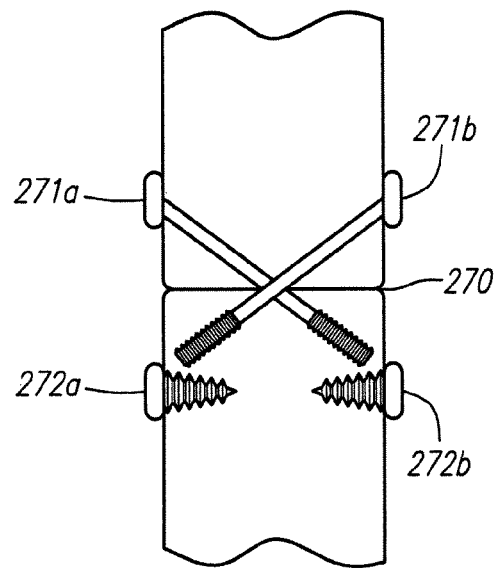
FIG. 15A is a partial coronal cross section through a joint between two bones illustrating an alternative embodiment of the invention.
Figure 15B:
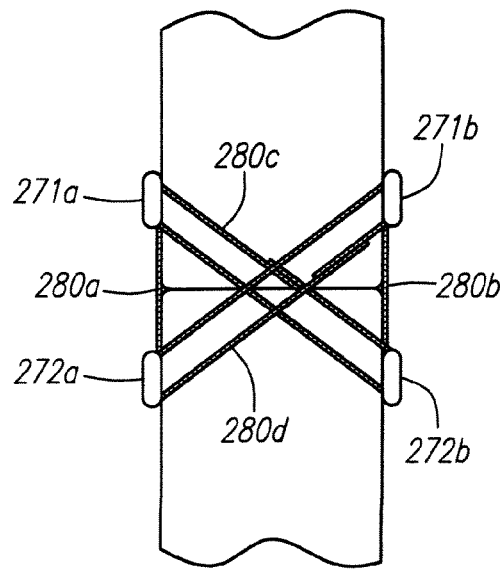
FIG. 15B is a posterior view of the embodiment of FIG. 15A showing suture bands placed around the screws to create diagonal and vertical fixation arms.

FIG. 15A is a partial coronal cross section through a joint between two bones illustrating an alternative embodiment of the invention. Here, two screws 271a,b have been placed across the joint 270. Screws 272a,b were also placed in the bone of the distal half of the joint 270. FIG. 15B is a posterior view of the joint 270 showing suture bands 280a-d placed around the screws 271a and 272b, 271a and 272a, 271b and 272a, and 271b and 272b to create diagonal and vertical fixation arms holding the bones around the joint together. The invention may be used to fuse joints in the axial skeleton or the extremities. The invention is particularly useful for fusing the joints of the hand or foot.

Figure 16A:
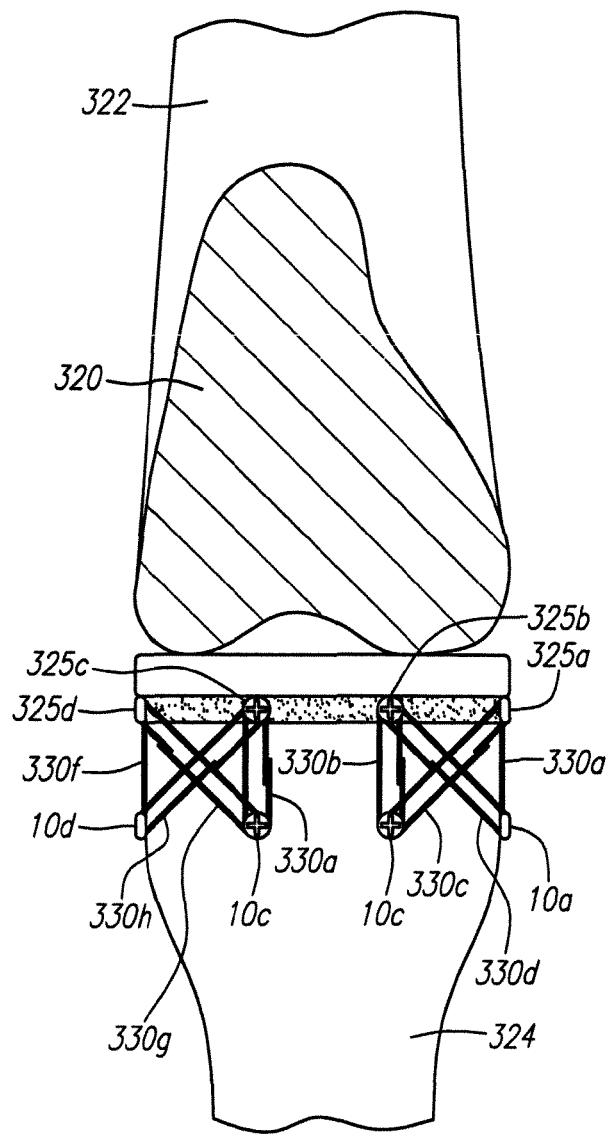
FIG. 16A is an anterior view of a prosthetic knee illustrating an alternative embodiment of the invention.

FIG. 16A is an anterior view of a prosthetic knee 320, a portion of the femur 322, a portion of the tibia 324 and an alternative embodiment of the invention. Anchors 10a-d, as previously described, were inserted into the anterior, medial, and lateral portions of the proximal tibia 324. T-shaped projections 325a-d extend from the anterior, medial, and lateral portions of the tibial portion of the knee replacements. Suture bands 330a-h were placed over the T-shaped projections 325a-d and the anchors 10a-d. Tension on the bands 330a-h compresses the tibial component of the prosthetic knee 320 against the tibia 324. The invention facilitates bone in-growth into the tibial component. The invention also reduces movement between the tibial component and the tibia 324. The t-shaped members 325a-d, the anchors 10a-d, and/or the sutures 330a-h may be resorbable. One or more resorbable component reduces the risk of particle debris. The resorbable component ideally maintains its ability to resist the forces applied to the component for at least two to three months.

Figure 16B:
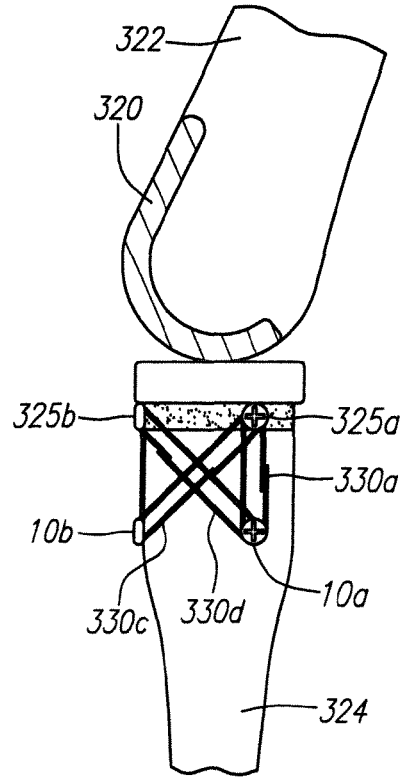
FIG. 16B is a lateral view the embodiment shown in FIG. 16A.

FIG. 16B is a lateral view of the prosthetic knee 320, a portion of the femur 322, a portion of the tibia 324, and the embodiment of the invention drawn in FIG. 16A. The invention could be used to fasten other prosthetic components of other parts of the body including other bones.

Band and Welding Tools

In some embodiments a suture banding tool may be used to position one or more sutures in a looped configuration around two anchors. For example, in some embodiments, once first and second anchors have been inserted into first and second vertebrae, a suture banding tool comprising a welding tool, a suture holding device and at least one suture held in the holding device can be advanced adjacent to the first and second anchors. The banding tool is positioned such that a looped portion of the suture extending from the distal end of the suture holding device can be placed around the shaft of the first and second anchors. First and second ends of the suture extend through the banding tool such that tension can be applied to the first and second ends, for example via a ratcheting mechanism located on the proximal end of the banding tool, to tighten the looped portion around the first and second anchors. Once the looped portion of the suture has been tightened around the anchors, the overlapping ends of the suture are welded together via the suture welding tool to form a suture band, or loop, connecting the first and second anchors. The suture ends are cut from the suture band and then the suture banding tool and suture ends are withdrawn.

Figure 3A:
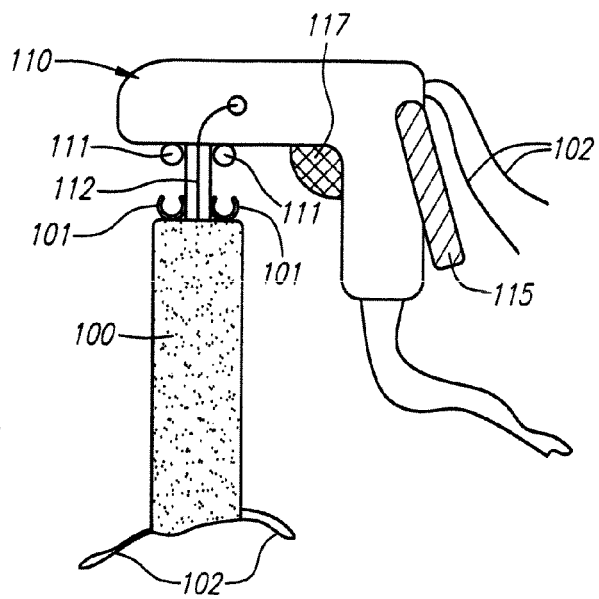
FIG. 3A is a lateral view of an embodiment of a suture holding tool releasably fastened to a suture welding tool.

FIG. 3A is a lateral view of a suture holding device releasably or reversibly fastened to a welding instrument. The holding tool 100 may be fastened to any suitable commercially available welding instruments. For example, as shown in FIG. 3A, the welding instruments supplied by Axya Medical (Beverly, Mass.) can be used with this embodiment of the invention. Here, clamps 101 located at the proximal end of the holding tool 100 attach to (by frictionally engaging) protrusions 111 located on the welding tool 100 to enable reversible fastening of the holding tool 100 to the welding tool 110 such that the shaft 112 of the welding tool is positioned in the lumen of the holding tool 100. The suture holding tool 100 holds a piece of suture 102 in a "banded" or "looped" configuration. The loops of the banded suture 102 are seen extending from the sides of the distal end of holding tool 100. The ends of the suture 102 pass through or along the holding tool 100 and attach to the welding instrument 110. The welding instrument 110 includes a ratcheting mechanism 115 that can apply tension to the ends of the suture 102 to decrease the size of the suture band once the loops of the band have been placed around anchors. The welding instrument 110 preferably has a feature to feed suture 102 into the holding tool 100 to increase the size of the suture band as needed to place it around the anchors. The welding instrument 110 holds tension on the ends of the suture, welds the suture, and cuts the ends of the suture distal to the weld. A trigger 117 may be used to turn on a heating element positioned on a shaft 112 in the distal region of the holding tool 100 to weld the sutures together.

Figure 3B:
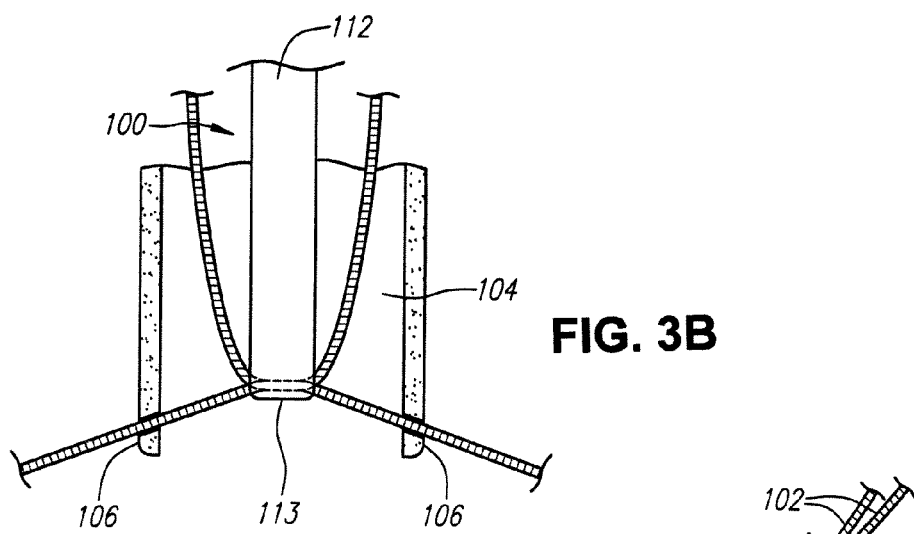
FIG. 3B is a lateral view of a sagittal cross-section through the embodiment of FIG. 3A.

FIG. 3B is a lateral view of a sagittal cross section through a portion of the band forming tool and a portion of the welding instrument drawn in FIG. 3A. The suture holding tool 100 is an elongate tubular member having a lumen 104 therethrough. The shaft 112 of welding instrument 110 is disposed within the lumen 104. The ends of the banded suture 102 course through the lumen 104, between the shaft 112 of the welding instrument and the walls of the suture forming tool 100. The ends of the suture have been passed through the tip or distal region 113 of the shaft 112 of the welding instrument to form a loop. The looped region of the suture extends out of and is held within notches or slots 106 located at the distal end of elongate tubular member 100.

Figure 3C:
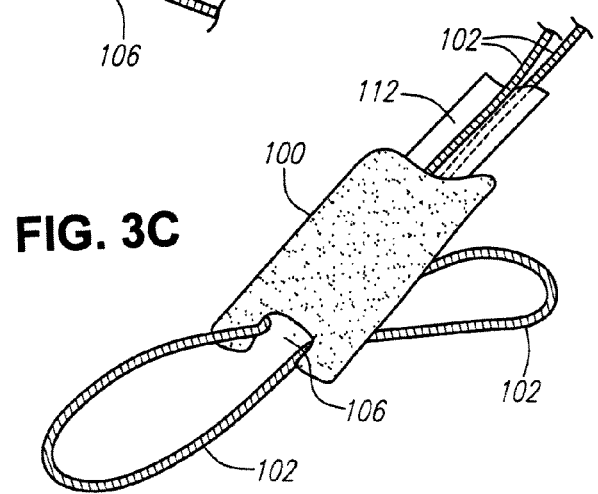
FIG. 3C is an oblique view of the embodiment of FIG. 3A showing a suture loop extending through a notch in the distal region.

FIG. 3C is an oblique view of the tip of the embodiment of the invention drawn in FIG. 3A and a loop of suture. The tool 100 holds the suture in the banded configuration. The shaft 112 of the welding instrument can be seen within the tool. The suture travels along the shaft 112 of the welding tool 110. The suture holding tool 100 preferably has an outer diameter, or width, of about 5 to about 12 mm. Alternatively, the suture holding tool 100 could have an outer diameter of about 2, about 3, about 4, about 13, about 14, or more millimeters. The inner diameter, or width, of the suture holding tool 100 is preferably about 3 to about 10 mm. Alternatively, the inner diameter of the suture holding tool 100 could be about 2, about 11, about 12, about 13, or more millimeters. The inner diameter of the suture holding tool 100 is preferably large enough to accommodate the shaft 112 of the welding instrument. Alternatively, the shaft 112 of the welding instrument could course outside, possibly through a slot or opening, in the shaft of the tool 100. The tool 100 is preferably about 10 to about 50 mm long. Alternatively, the tool can be about 5, about 6, about 7, about 8, about 9, about 51, about 52, about 53, or more millimeters long. The suture holding tool 100 is preferably made of clear plastic. Clear plastic enables surgeons and their assistants to view the shaft of the welding instrument and the sutures. Alternatively, the suture holding tool 100 could be made of metal, or other material. The suture holding tool 100 is preferably supplied to hospitals with one or more preloaded sutures in the banded configuration. In some embodiments, the suture holding tool 100 may be reloaded with sutures by the scrub nurse.

Figure 3D:
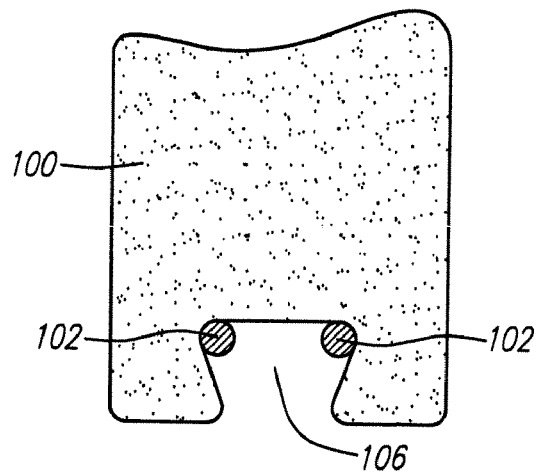
FIG. 3D is a lateral view of the distal region of the embodiment in FIG. 3A.

FIG. 3D is a lateral view of the tip of the embodiment of the invention drawn in FIG. 3C and a cross section of the suture loop extending from the tool 100. The sides of the tip of the tool 100 have two slots 106 to hold the suture in the banded configuration. The walls of the slots 106 are preferably slanted to help hold the suture 102 band near the base of the slot. The slots 106 are preferably about 2 to about 6 mm wide. Alternatively, the slot 106 may be about 1, about 7, about 8, about 9, or more millimeters wide. The slots 106 are preferably about 1 to about 5 mm deep. Alternatively the slots 106 may be less than 1 mm deep or alternatively about 6, about 7, about 8, or more mm deep.

Figure 3E:
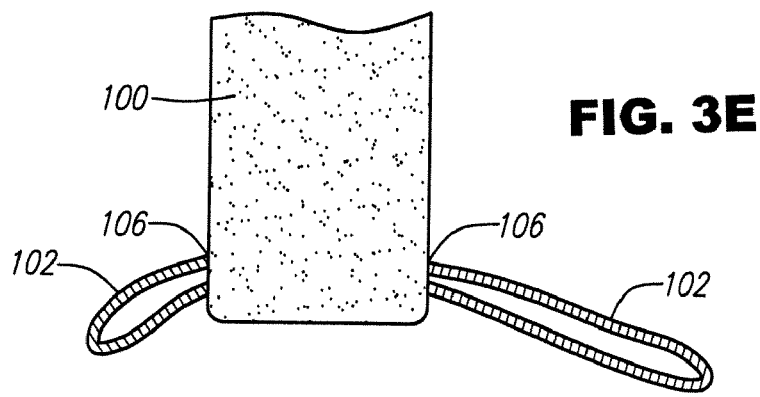
FIG. 3E is an anterior view of the distal region of the embodiment in FIG. 3A.

FIG. 3E is an anterior view of the tip of the embodiment of the invention drawn in FIG. 3C. The two loops of the banded suture 102 can be seen extending through the slots 106 on the side of the tool 100. The tool 100 preferably directs the loops of suture 102 to the sides of the tool 100 and distal to the tip of the tool 100.

Figure 3F:
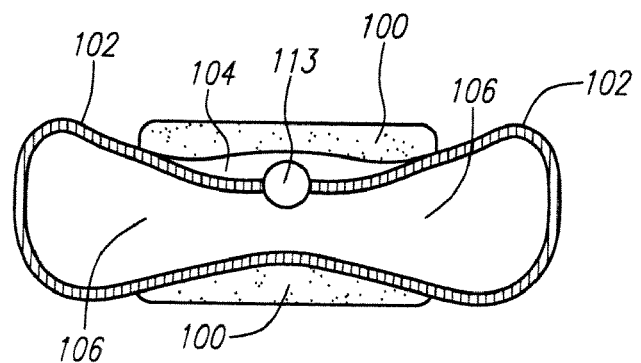
FIG. 3F is a cross-section of the distal end of the embodiment in FIG. 3A showing suture loops extending through slots in the distal region of the suture holding tool.

FIG. 3F is a view of the end of the embodiment of the invention drawn in FIG. 3A. The walls of the distal end of elongate tubular member 100 hold the suture in the banded configuration by preventing the suture from expanding in all directions, forcing the suture to form a narrow loop by confining the suture loop to a narrow width (i.e., the diameter of the lumen 104) while allowing the suture to exit the lumen 104 through slots 106. Nylon sutures are preferably used in this embodiment of the invention. The stiffness of the nylon suture causes the suture to press against the sides of the band forming tool. The tool could be configured to accept 3-0 to #5 size suture. Alternatively, a smaller tool could be used with smaller diameter sutures and larger tools could be used with larger diameter sutures. In some embodiments, the suture holding tool may be used to form bands with other flexible materials. For example, the suture holding tool could be used to form bands with multi-filament materials such as polyester suture, braided polyethylene, and metal cables. The slots 106 from the side of the tool are preferably configured to hold the suture band in a "bowtie" shape. The large loops of the suture 102 facilitate placement of the suture band over the enlarged ends (e.g., washers, T-anchors, transverse components, etc.) of the anchors. The ends of the suture course through the distal tip 113 of the shaft 112 of the welding tool.

Figure 3G:
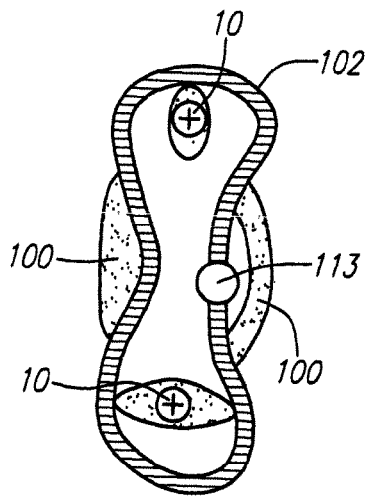
FIG. 3G a cross-section of the distal end of the embodiment in FIG. 3F showing suture loops placed around two anchors.

FIG. 3G is an anterior view of a cross section through the tip of the band forming tool drawn in FIG. 3A with the suture loop extended around two anchors 10a,b. The loops of the suture band 102 are placed over the washers of the anchors 10a,b. The tool 100 preferably forms suture bands that are about 10 to about 100 mm long. Alternatively, the tool 100 can form bands about 3, about 4, about 5, about 6, about 7, about 8, or about 9, or less millimeters long. Alternatively, the tool can form bands about 101, about 102, about 103, about 104, or about 105 millimeters long. The tool preferably forms bands about 2 to about 12 mm wide, alternatively about 5 to about 10 mm wide. Alternatively, the tool could form bands about 1, about 13, about 14, about 15, about 16 or more millimeters wide. The length and width of the bands may be adjusted by forcing additional suture through the slots 106 of the tool 100 or pulling suture through the slots 106 of the tool 100.

Figure 3H:
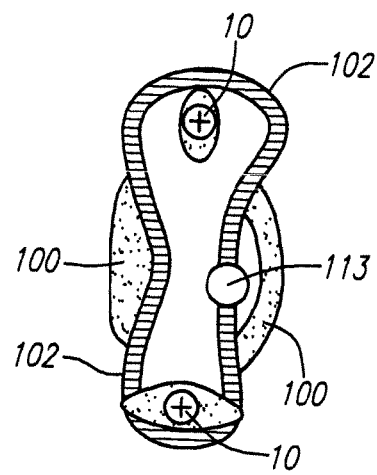
FIG. 3H a cross-section of the distal end of the embodiment in FIG. 3G showing suture loops tightened around the shafts of the two anchors FIG. 3I a cross-section of the distal end of the embodiment in FIG. 3H showing suture loops further tightened around the shafts of the two anchors to bring the two anchors closer together

FIG. 3H is an anterior view of a cross section through the tip of the band forming tool drawn in FIG. 3G. The band of suture 102 has been passed over the washers of the anchors 10a,b. The length and width of the band 102 has been reduced by tension on the ends of the suture. Surgeons preferably use the welding tool 110 to apply tension to the ends of the suture. The suture band 102 passes around the shafts of the anchors 10a,b. Washers on the head of the anchors 10a,b hold the suture band 102 against the shafts of the anchors 10a,b.

Figure 3I:
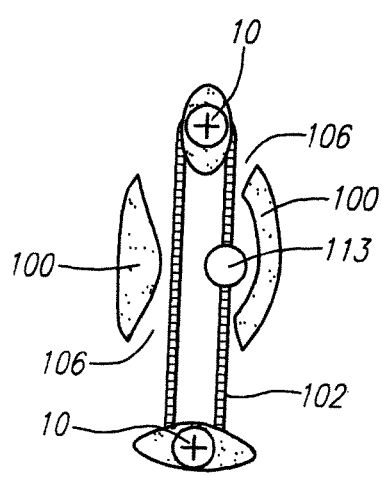
FIG. 3J is a lateral view of the distal region of the embodiment in FIG. 3H showing the suture band released from the slots in the suture holding tool.
FIG. 3K is a lateral view of the embodiment in FIG. 3A showing the mechanism for releasably attaching the suture holding tool to a suture welding tool.
Figure 3J:
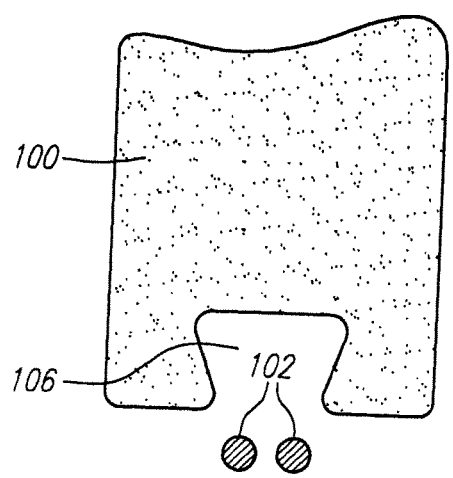

FIG. 3I is an anterior view of a cross section through the tip of the band forming tool 100 drawn in FIG. 3G. The length and width of the suture band 102 has been further reduced by applying additional tension to the ends of the suture. Tension on the ends of the sutures may be used to bring the anchors 10a,b closer together. As discussed above, bringing the anchors 10a,b closer together applies compression to a device in the intradiscal space. The welding instrument welds the overlapping portions of the suture held in the distal tip 113 of the welding instrument together to create a suture band. The narrow suture band 102 no longer is held in the slots 106 of the band forming tool 100. The ends of the welded suture are cut, the welding tool released form the suture band, and both tools removed from the suture band. As shown in FIG. 3J the welded suture band 102 has been released from the band forming tool 100 and no longer lies within slot 106.

Figure 3K:
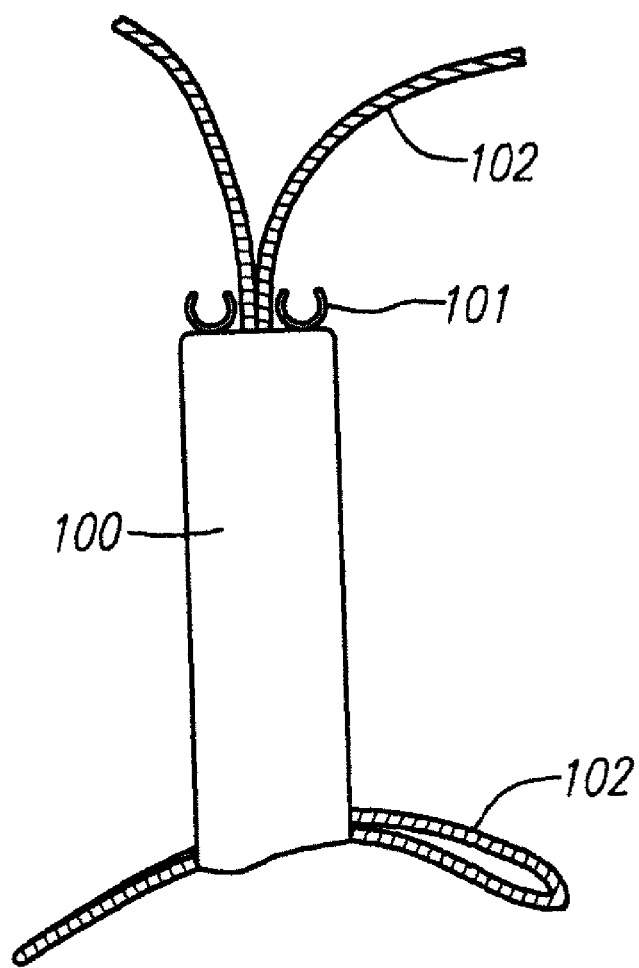

FIG. 3K is a lateral view of the embodiment the invention drawn in FIG. 3A. The band forming tool 100, with a pre-loaded suture 102, can be attached to a welding tool using clamps 101. The ends of the suture 102 can be attached to the welding instrument. In some embodiments, the device 100 could be supplied to hospitals preloaded with a banded suture 102. Alternatively, the suture holding tool may be preloaded with several suture bands. In some embodiments, the suture holding tool 100 could include a self-loading feature. Alternatively, the suture holding tool 100 may have a spool loaded with suture. Suture could be pulled from the tool to form additional suture bands. The device could be attached to welding instruments in the operating room. The device is preferably disposable.

Figure 4A:
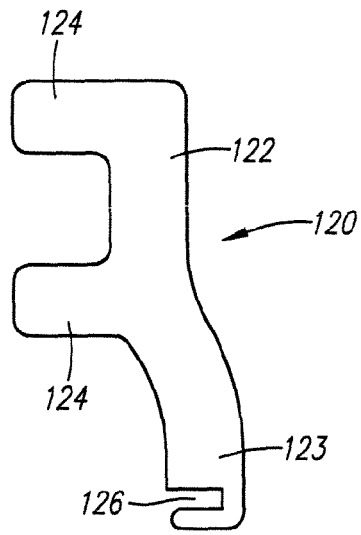
FIG. 4A is a lateral view of an alternative embodiment of a suture banding tool.

FIG. 4A is a lateral view of an alternative band tool. The suture holding device 120 can be releasably mounted onto a welding tool. The upper portion of the suture holding device 120 can frictionally engage the shaft of the suture welding tool. The suture holding device 120 has an elongate member 122 with at least two curved extensions 124 that extend from opposite sides of the elongate member 122 and are adapted to frictionally engage a circular or curved welding tool. The welding tool and the suture holding tool may have features to increase the friction between the components. For example, one or both components may have teeth, knurled, or other textured opposing surfaces. Such features help prevent rotation of the band tool about the welding tool. In one embodiment, the elongate member 122 may have four curved extensions 124 that extend from opposite sides of the elongate member 122. The distal region 123 of the elongate member is preferably curved such that when the suture holding device 120 is attached to the welding tool, the distal end of the elongate member 122 extends a fixed distance from the distal end of the welding tool (or the portion of the welding tool through which the sutures pass through). Furthermore, the distal region has a recess or notch 126 adapted to receive the suture. The recess is preferably about 2 to about 4 mm deep. Alternatively, the recess may be about 1 mm or less deep. Alternatively, the recess may be about 5, about 6, or about 7 or more millimeters deep. The recess is preferably about 1 to about 2 mm tall. Alternatively, the recess may be less than about 1 millimeter tall, or about 3, or about 4 or more millimeters tall.

Figure 4B:
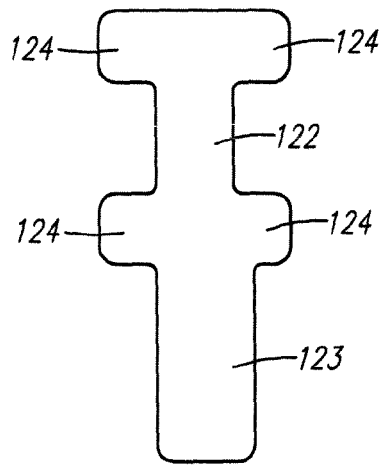
FIG. 4B is an anterior view of the embodiment in FIG. 4A
Figure 4C:
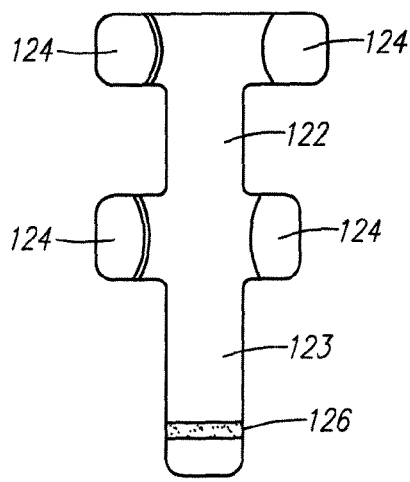
FIG. 4C is a posterior view of the embodiment in FIG. 4A.
Figure 4D:
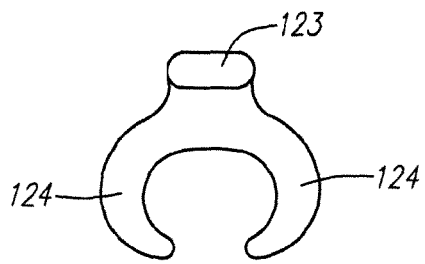
FIG. 4D is a view of the distal end of the embodiment in FIG. 4A.

FIG. 4B is an anterior view of the embodiment of the invention drawn in FIG. 4A. The distal region 123 of the device is preferably about 1 to 10 mm wide. Alternatively, the distal region 123 of the device could be less than about 1 mm wide or alternatively, about 11, about 12, about 13, or about 14 or more millimeters wide. Tools with smaller widths may be used to form shorter bands. For example, tool with widths less than about 8 mm may be used to form bands about 4 to about 26 mm long. Tools with widths of about 8 to about 16 mm may be used to form bands about 20 to about 40 mm long. Tools with widths of more than about 16 mm may be used to form bands more than about 40 mm long. FIG. 4C is a posterior view of the embodiment of the invention drawn in FIG. 4A. FIG. 4D is a view of the distal end of the embodiment of the invention drawn in FIG. 4A illustrating the curved extensions 124 extending from the elongate member 122.

Figure 5A:
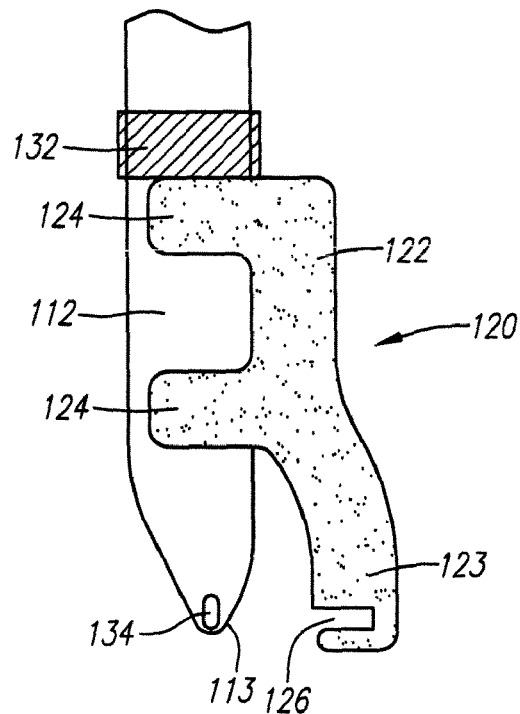
FIG. 5A is a lateral view of the embodiment in FIG. 4A releasably attached to a suture welding tool

FIG. 5A is a lateral view of the embodiment of the invention drawn in FIG. 4A and the shaft 112 of a welding tool. The suture holding device 120 was fastened to the side of the shaft 112 of the welding tool. The shaft 112 of the welding tool has band 132 with a diameter larger than the diameter of the shaft 112 of the welding tool. The suture holding device 120 is placed just below the band 132. Alternatively, the device 120 could be fastened to the handle of the welding tool. One such fastening method is illustrated in FIG. 5A. Alternative mechanisms may be used fasten the suture holding device 120 to the shaft 112 or the handle the welding tool. The slot 126 of suture holding device 120 preferably aligns with the opening or aperture 134 for the suture in the welding tool. The tip or distal region 123 of suture holding device 120 is preferably about 3 to about 6 mm from the tip 113 of the welding tool. Alternatively the tip or distal region 123 of suture holding device 120 may be about 1, about 2, about 7, about 8, about 9 or more millimeters from the tip 113 of the welding tool. The opening or aperture 134 in the welding tool may lie distal or proximal to the slot 126 of the suture holding device 120.

Figure 5B:
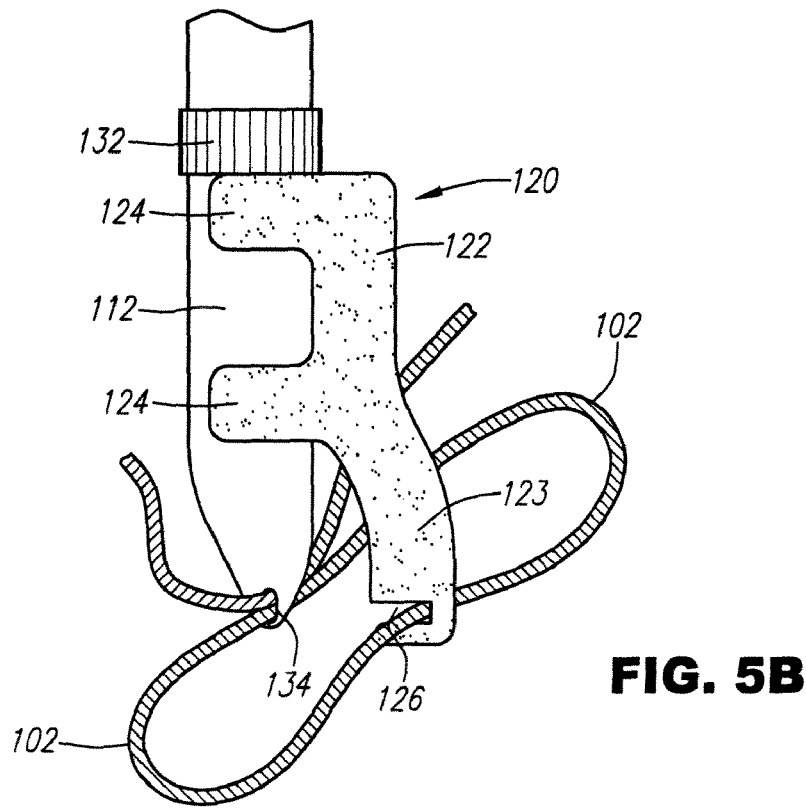
FIG. 5B is a lateral view of the embodiment in FIG. 5A showing a suture loaded onto the tool such that suture loops extend from the distal ends of the holding tool and the welding tool.

FIG. 5B is a lateral view of the embodiment of the invention drawn in FIG. 5A loaded with a suture. A suture 102 has been placed into the hole or aperture 134 through the welding tool and also through slot 126 of suture holding device 120. The stiffness of the suture forces the suture 102 into slot 126 forming a suture loop extending from the aperture 134 and the slot 126.

FIG. 5C is a lateral view of the embodiment of the invention drawn in FIG. 5B and an elevation view of anchors. The "banded" suture 102 has been placed around the shaft of anchors 10a,b. Tension has been applied to the ends of the suture 102 to tighten the suture band around the anchors 10a,b. The suture 102 has pulled out of slot 126 as the suture band narrowed.

FIG. 5D is an exploded view of the embodiments of the invention drawn in FIG. 5C and an anterior view of a portion of the spine. Overlapping ends of the suture 102 have been welded after fully tightening the suture band around anchors 10. The ends of the suture were cut on either side of the weld. The ends of the suture, the welding tool, and the suture holding device 120 are removed after cutting the suture.

Figure 5E:
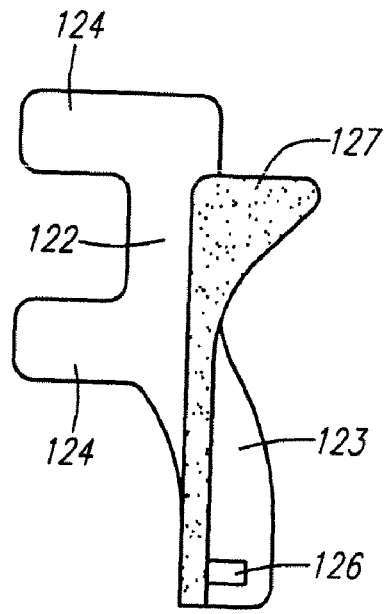
FIG. 5E is a lateral view of an alternative embodiment of a suture banding tool having a retractable component.

FIG. 5E is an alternative suture holding device with a retractable component. Retractable component 127 has been advanced distally to cover slot 126 in the curved distal region 123 of the band forming tool. Retractable component 127 is advanced distally, after the suture loop has been placed in the slot 126 of the band forming tool. Retractable component 127 prevents the suture band from prematurely exiting the slot 126 in the band forming tool. The retractable component may be incorporated into several of the inventions described in other band tools or suture holding devices.

Figure 5F:
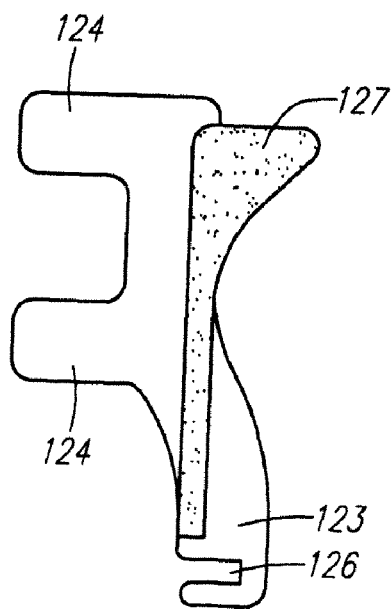
FIG. 5F is a lateral view of the embodiment in FIG. 5E showing the retractable component retracted to release the suture.

FIG. 5F is a lateral view of the embodiment of the invention drawn in FIG. 5E. Retractable component 127 has been pulled in a proximal direction. Such movement enables the suture to slide out of the slot 126 as the suture is tightened and welded. Retractable component 127 may be spring loaded. Spring loaded embodiments of the invention hold the retractable component in an "open" or "closed" position until the component is manipulated. The device may be configured to retract as tension is applied to the ends of the suture.

Figure 6A:
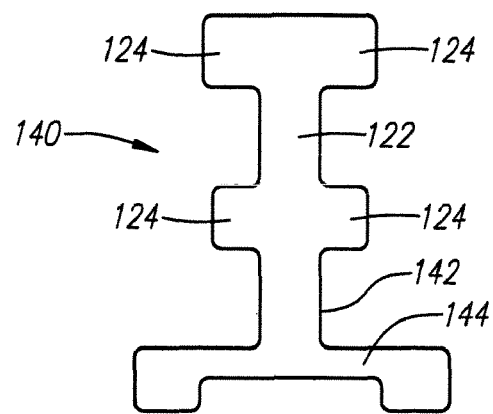
FIG. 6A is an anterior view of an alternative embodiment of a suture banding tool.

FIG. 6A is an anterior view of an alternative suture holding device. The suture holding device 140 can be releasably mounted onto a welding tool. The upper portion of the suture holding device 140 can frictionally engage the shaft of the suture welding tool. The suture holding device 140 has an elongate member 122 with at least two curved extensions 124 that extend from opposite sides of the elongate member 124 and are adapted to frictionally engage a circular or curved shaft of a welding tool. In one embodiment, the elongate member 122 may have four curved extensions 124 that extend from opposite sides of the elongate member 124. The distal region has an elongate transverse member 144 with at least one recess at each end that is adapted to releasably hold a suture. In one embodiment, elongate transverse member 144 has at least two recesses at each end that are adapted to releasably hold a suture. The elongate transverse member 144 is preferably about 5 to about 15 mm wide. Alternatively, the elongate transverse member 144 could be about 2, about 3, about 5, about 16, about 17, or about 18 or more millimeters wide. The tool may be used to form bands longer than the bands formed by the tool drawn in FIG. 5A. The stiffness of transverse member 144 helps surgeons manipulate the suture loop against the soft tissues of surgical wounds.

Figure 6B:
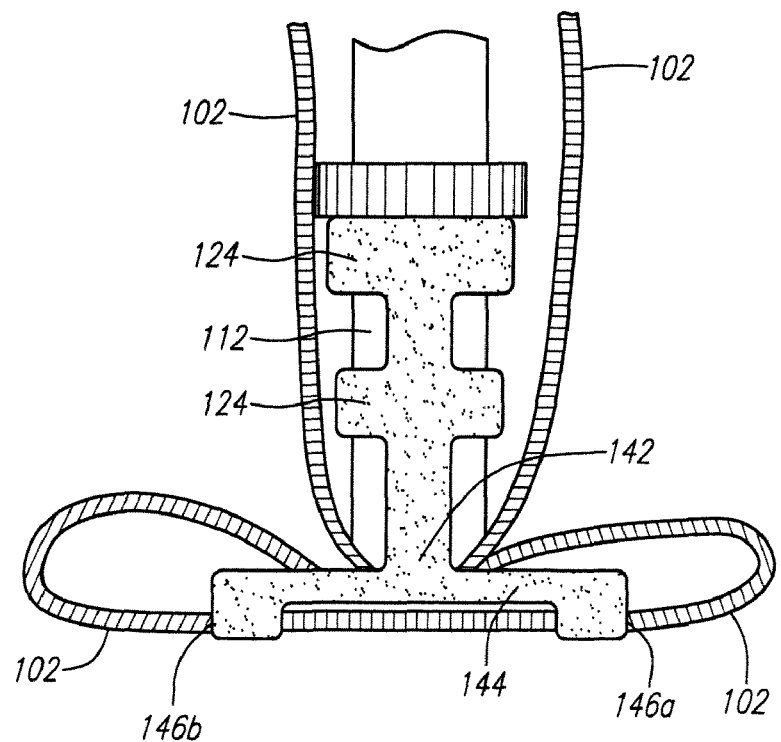
FIG. 6B is an anterior view of the embodiment of FIG. 6A releasably attached to a welding tool and loaded with a suture such that the suture forms loops extending from the distal region of the suture banding tool.

FIG. 6B is an anterior view of the embodiment of the invention having at least two recesses 146, including a suture 102, and the shaft 112 of the welding tool. Elongate transverse member 144 has least one recess 146 at either end to separate the suture and form the loop. The suture 102 is "banded" by cooperation between the two slots 146a,b in the device located at either end of the elongate transverse member 144 and the jaws of the welding tool 112.

Figure 6C:
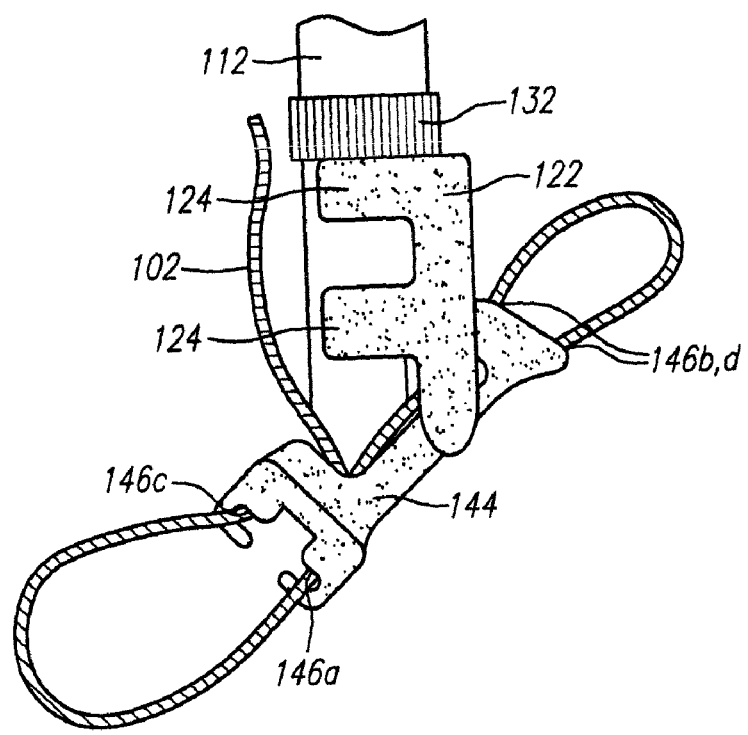
FIG. 6C is an oblique view of an alternative embodiment of the suture banding tool illustrated in FIG. 6A having four recesses for holding a suture.

FIG. 6C is an oblique view of the embodiment of the invention the invention having at least four recesses 146, including a suture 102, and the shaft 112 of the welding tool. Elongate transverse member 144 has least two recesses 146a,b,c,d at either end to separate the suture 102 and form the loop. The suture 102 is "banded" by cooperation between the slots 146a,b,c,d in the device 140 located at both ends of the elongate transverse member 144 and the jaws of the welding tool 112.

Figure 7:
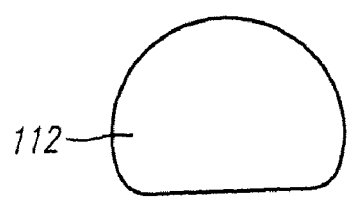
FIG. 7 is a cross-sectional view of the shaft of a suture welding tool.

FIG. 7 is a cross section of the shaft of a welding tool. The shaft 112 of the tool is preferably non-circular in cross section. Such shape minimizes rotation of the suture holding devices about the shaft 112 of the welding tool.

Figure 8:
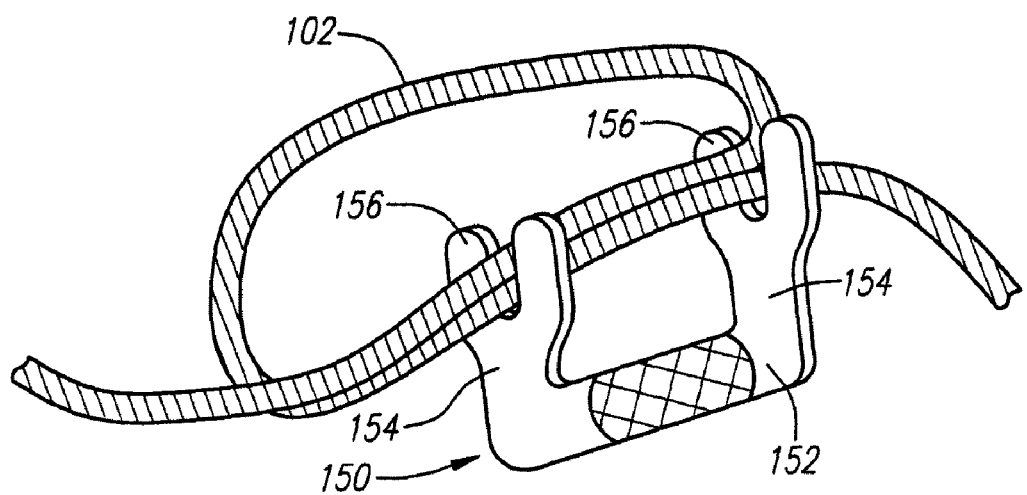
FIG. 8 is an oblique view of an embodiment of a suture loading tool.

FIG. 8 is an oblique view of a suture loading tool. Suture loading device 150 holds a suture 102 in a banded configuration. Device 150 includes an elongate member having two extensions 154 with slots 156 at their distal ends that are adapted to receive the suture. The extensions 154 with slots 156 align and hold the overlapped portions of the suture 102. The device is used to reload the embodiments of the invention drawn in FIGS. 13 and 15. Suture loading device 150 is pulled off the banded suture 102 after the overlapped portions of suture are contained within the jaws of the welding tool.

FIG. 9A is a view of the proximal end of an alternative suture loading device. FIG. 9C is a lateral view and FIG. 9D is an anterior view of FIG. 9A. Suture loading device 160 includes two U-shaped devices. The larger U-shaped portion has slots 162 at the distal ends of the legs. The smaller U-shaped portion has slots 163 at the distal ends of the legs and is connected to the larger U-shaped device at the middle portions of the U-shaped devices. The slots 162, 163 in the elastic device releasably hold suture in the banded configuration.

FIG. 9B is a view of the proximal end of the embodiment of the invention drawn in FIG. 9A and a banded suture. Suture loading device 160 is use to reload the embodiments of the invention drawn in FIGS. 4 and 6. Suture loading device 160 is pulled off the banded suture 102 after the overlapped portions of suture are contained within the jaws of the welding tool. The portion of the suture contained in slots 163 in the narrow portion of the device expands outward as the device is removed from the suture. The suture 102 becomes trapped in the lateral slot or slots of the suture holding devices, respectively, as the suture band widens or expands outward.

Figure 10A:
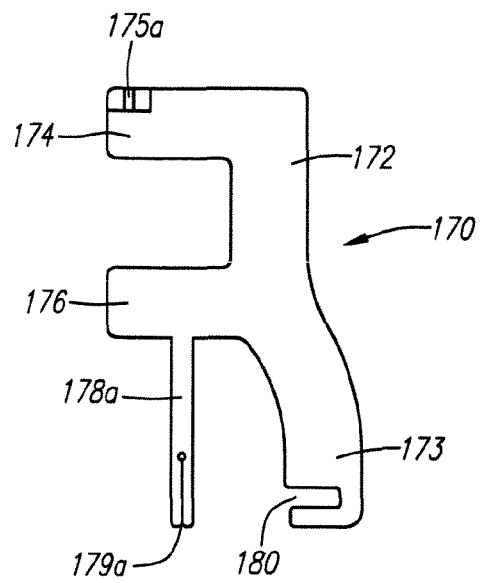
FIG. 10A is a lateral view of an alternative embodiment for a suture banding tool that can be releasably attached to a suture welding tool.
Figure 10B:
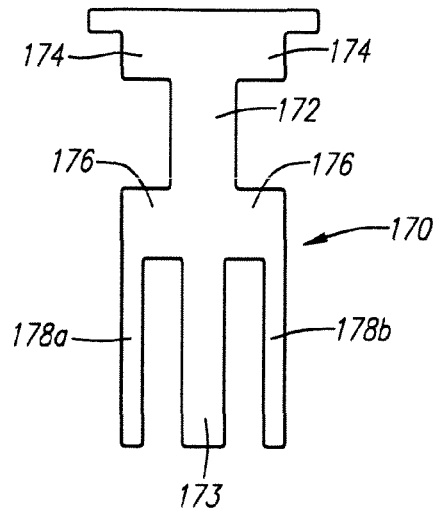
FIG. 10B is an anterior view of the embodiment of FIG. 10A.

FIG. 10A is a lateral view of an alternative suture holding device that can be releasably attached to the shaft of a welding tool. FIG. 10B is an anterior view of the embodiment of the invention drawn in FIG. 10A. The upper portion of the suture holding device 170 can frictionally engage the shaft of the suture welding tool. The suture holding device 170 has an elongate member 172 with at least two curved extensions 174, 176 that extend from opposite sides of the elongate member 174 that are adapted to frictionally engage a circular or curved welding tool. Curved extensions 174 extend from a proximal or top portion of elongate member 172 and each have notch 175 adapted to releasably retain the suture. Curved extensions 176 extend from a mid region of elongate member 172 and each have a vertical extension that extends from the curved extension 176 vertically downward. Vertical extensions 178 have a notch 179 at their distal ends that are adapted to releasably retain the suture. The distal region 173 of elongate member 172 is preferably curved such that when the suture holding device 170 is attached to the welding tool, the distal end of the elongate member 172 extends a fixed distance from the distal end of the welding tool (or the portion of the welding tool through which the sutures pass through). Furthermore, the distal region 173 has a recess or notch 180 adapted to receive the suture.

Figure 10C:
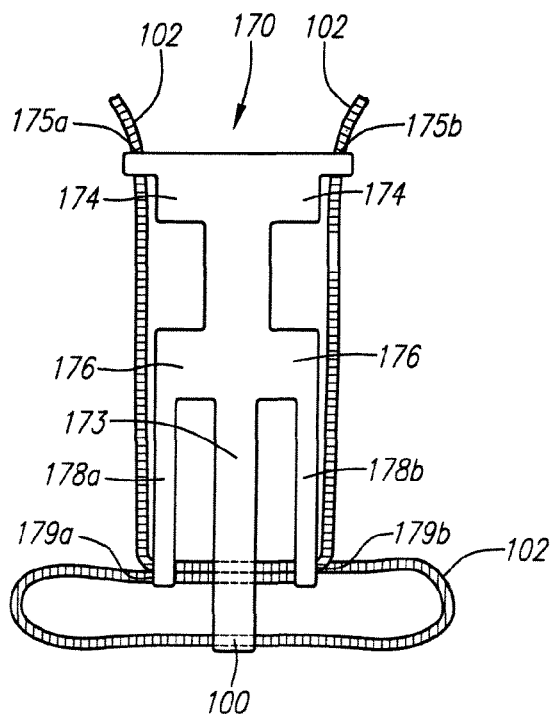
FIG. 10C is an anterior view of the embodiment in FIG. 10A loaded with a suture formed into a band.

FIG. 10C is an anterior view of the embodiment of the invention drawn in FIGS. 10A and B and a suture. The suture 102 has been weaved through device 170 to create a suture band. At the top portion of the device 170, suture 102 is passed through notches 175, extending downward to pass through notches 179 in vertical extensions 178 and notch 180 is the curved distal region 173 of elongate member 172. The suture overlaps between the vertical extensions 179. Suture holding device 170 and banded suture 102 may be fastened to the shaft of a welding tool. Multiple such devices may be supplied to surgeons during surgery. The surgeons may reload the welding tool after applying a suture band to the patient. The welding tool is reloaded by removing and discarding the device after placement of a suture band followed by fastening a device with a new banded suture. Suture holding device 170 speeds surgery by banding the suture for the surgeon and by aligning the overlapping portions of the suture. Previous methods require surgeons to overlap and carefully align the suture ends before placing the overlapping portions of the suture in the jaws of the welding tool. Small tolerances are used between the jaws to the welding tool and the overlapping portions of the suture. The device may be supplied with suture bands of various predetermined lengths. For example, a first device ("Size 1") may supply bands about 10 mm or less in length. A second device ("Size 2") may supply bands about 20 mm or less in length. A third device ("Size 3") may supply bands about 30 mm or less in length. A fourth device ("Size 4") may supply bands about 40 mm or less in length. A fifth device ("Size 5") may supply bands about 50 mm or less in length. A sixth device ("Size 6") may supply bands about 60 mm or less in length. A seventh device ("Size 7) may supply bands about 70 mm or less in length. An eighth device ("Size 8") may supply bands about 80 mm or less in length. A ninth device ("Size 9") may supply bands about 110 mm or less in length. A tenth device ("Size 10") may supply bands about 120 mm or longer. The loops at the ends of the bands are preferably about 5 to about 15 mm wide. Alternatively, the loops at the ends of the bands may be about 2, about 3, about 4, about 16, about 17, or about 18 or more millimeters wide. The bands may be supplied in more sizes than previously listed. For example, the bands may be supplied with less than about 10 mm difference in length, or less than about 9 mm difference in length, or less than about 8 mm difference in length, or less than about 7 mm difference in length, or less than about 6 mm difference in length, or less than less than about 3 mm difference in length. For example, Size 1 may include bands about 7 mm in length. Size 2 may have bands about 10 mm in length, etc.

Figure 10D:
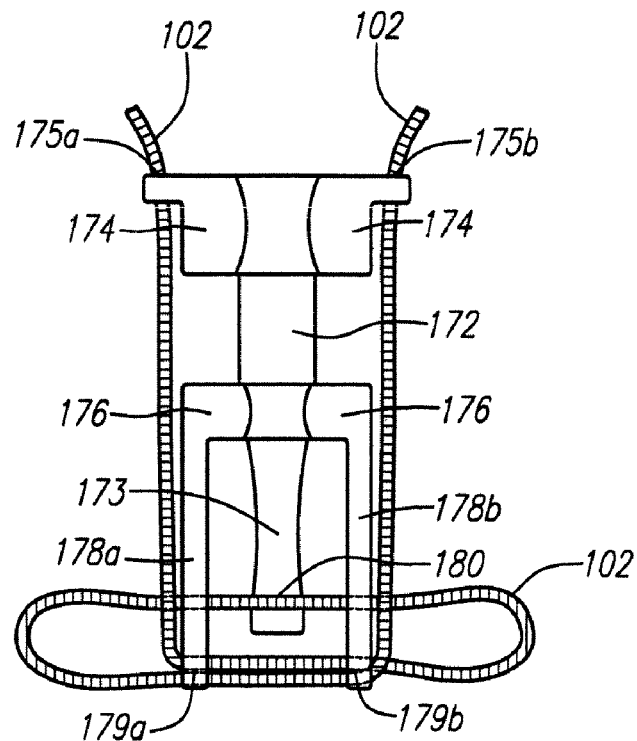
FIG. 10D is a posterior view of the embodiment in FIG. 10C.

FIG. 10D is a posterior view of the embodiment of the invention drawn in FIG. 19C. The ends of the suture 102 are fastened to the sides of the device through notches 175. The ends of the suture 102 are released from the sides of the device and fastened to the welding tool after the tip of the welding tool is placed around the overlapping portions of suture. The drawing illustrates perfect alignment of the overlapping portions of the suture.

Figure 10E:
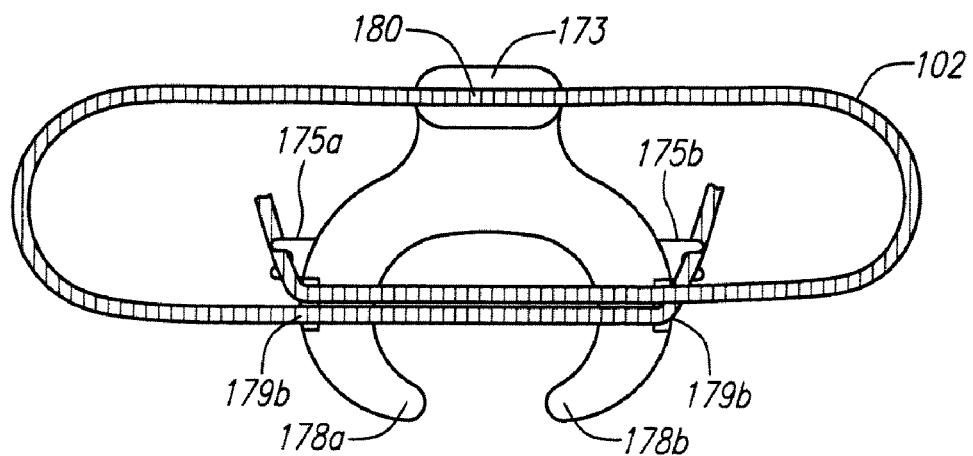
FIG. 10E is a view of the distal end of the embodiment of FIG. 10D.

FIG. 10E is a view of the distal end of the embodiment of the invention drawn in FIG. 10D. Slot 180 of the device contains one portion of the banded suture. The overlapped portions of the suture are contained by slots 179.

Figure 10F:
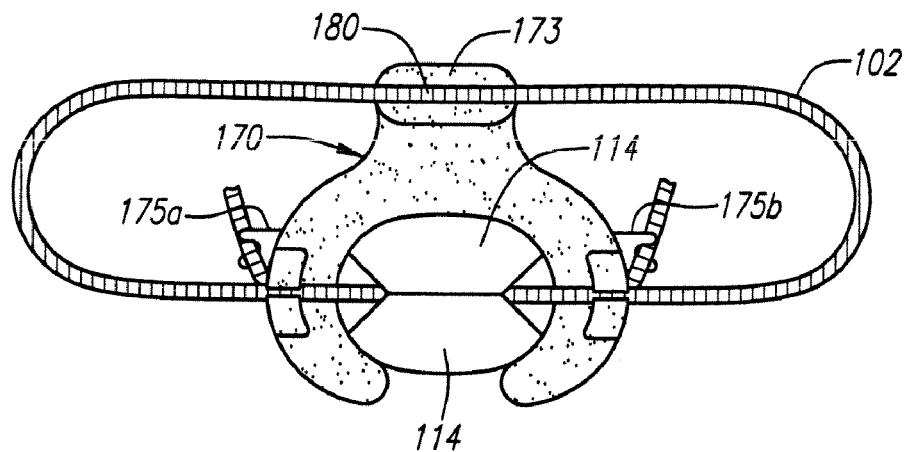
FIG. 10F is a view of the distal end of the embodiment of FIG. 10E showing the suture welding tool surrounding the overlapping portions of the suture.

FIG. 10F is a view of the distal end of the embodiment of the invention drawn in FIG. 10E and the tip of a welding tool. The jaws 114 of the welding tool surround the overlapped portions of suture 102. Suture holding device 170 is removed from the banded suture after placing the banded suture over two or more anchors, tightening the banded suture, welding or otherwise fastening the tightened suture and releasing the ends of the suture by cutting the suture on either side of the welded or otherwise fastened portion of the suture.

Figure 10G:
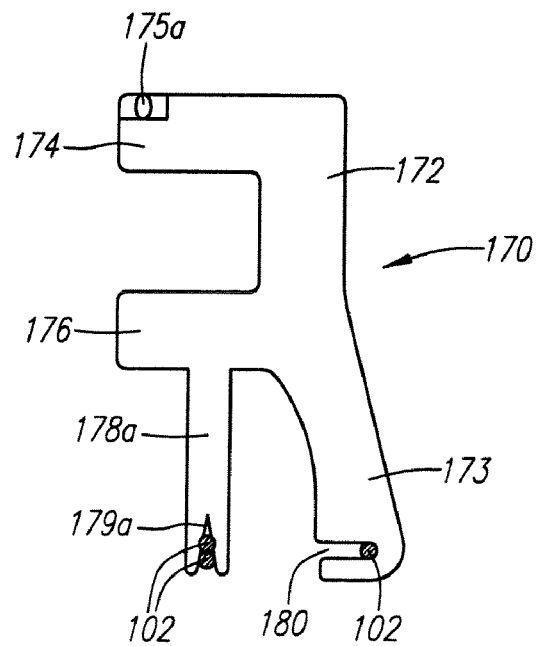
FIG. 10G is a lateral view of the embodiment of FIG. 10D.

FIG. 10G is a lateral view of the embodiment of the invention drawn in FIG. 10D and a cross section of the banded suture. Elasticity of the device enables the device to hold and release the overlapped portion of the suture.

Figure 10H:
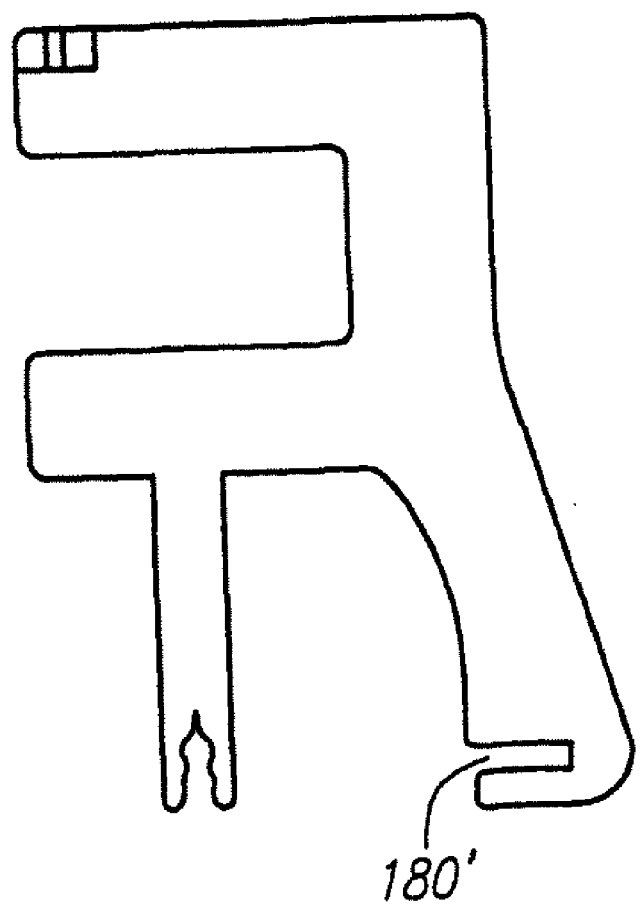
FIG. 10H is a lateral view of an alternative embodiment of a suture banding device wherein the top and bottom portions of the lateral slot have different lengths.

FIG. 10H is a lateral view of an alternative embodiment of the invention drawn in FIG. 10A. The top and bottom of slot 180' on the lateral portion of the device are different lengths.

FIG. 11A is a lateral view of an alternative suture holding device. Suture holding device or band tool 190 includes two elongate members 192, 194 connected together with an axle or hinge-like joint 195. The invention could be fastened to a welding tool (not shown). As seen in FIG. 11C, which depicts an end view of elongate member 192 or 194, the tips of the elongate members 192, 194 could have slots 196 that enable device 190 to cooperate with both sides of the suture loop, i.e., one of the elongate members 192, 194 engages the side of the loop with the overlapping sutures and the other engages the side of the loop with the single suture. Alternatively, the tips of elongate members 192, 194 could have slots that cooperate with one side of the suture loop, i.e., both of the elongate members 192, 194 engage the side of the loop with the overlapping sutures. The welding tool could be used to form and manipulate the one side of the suture loop in the last embodiment of the invention described in this text.

FIG. 11B is a lateral view of the embodiment of the invention drawn in FIG. 11A. The handle portions of the components 192, 194 were compressed. Compressing the handles separates the tips of elongate members 192, 194. One or both elongate members 192, 194 may have spring-loaded tips that grasp the suture. The spring loaded tips could be used to enlarge the suture band. Alternatively, the tips of the tool could separate and compress in a plane transverse to the long axis of the suture band.

Figure 11D:
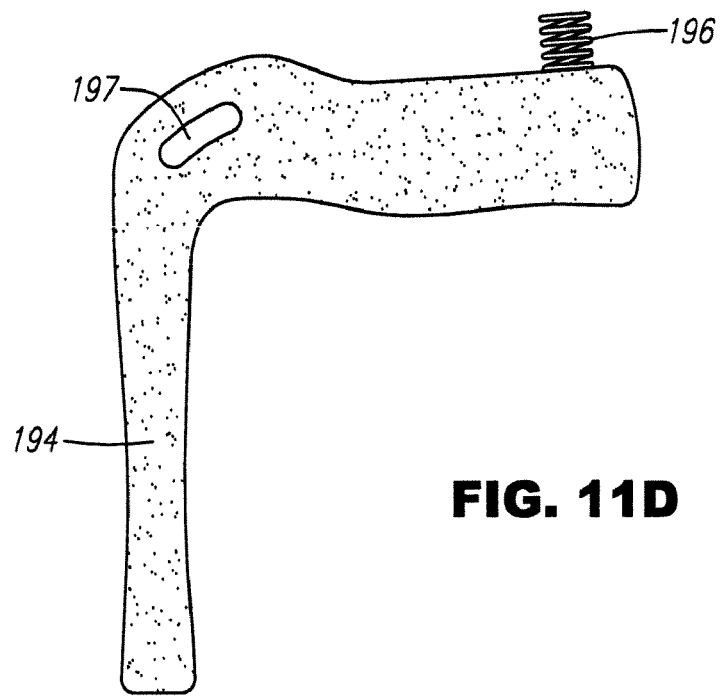
FIG. 11D is a lateral view of the one of the elongate members of FIG. 11B.

FIG. 11D is a lateral view of one of the components drawn in the embodiment of the invention drawn in FIG. 20B. The top of the elongate member 194 is cam shaped. The elongate member also has a spring 196 on the handle and a slot 197.

Figure 11E:
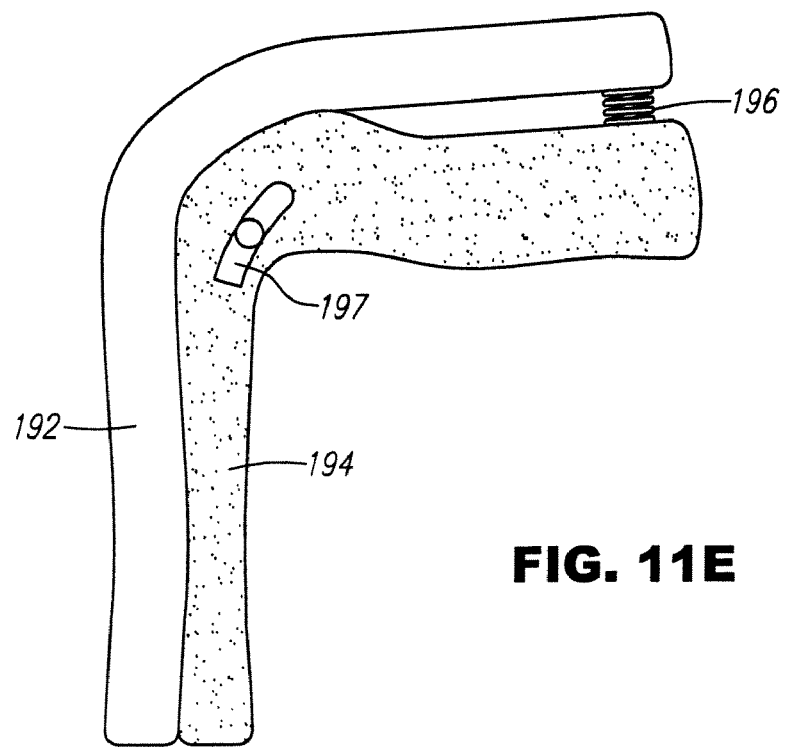
FIG. 11E is a sagittal cross-section of the embodiment of FIG. 11B.

FIG. 11E is a sagittal cross section of the embodiment of the invention drawn in FIG. 11B. The cam shape of elongate member 192 cooperates with the handle of elongate member 194 to advance the tip of the elongate member 192 as the handles of the two elongate members are compressed. The slot 197 in elongate member 192 also enables the tip of elongate member 192 to advance when the handles of the components 192, 194 are compressed.

Figure 12A:
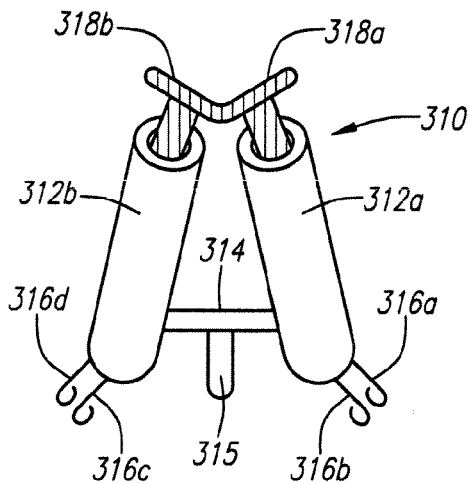
FIG. 12A is an alternative embodiment of a suture banding tool.

FIG. 12A is an anterior view of an alternative band forming tool. The device is drawn in its contracted position. The device includes two elongate tubular members 312a, b having proximal ends, distal ends, and lumens therethrough. The two elongate tubular members 312a, b are connected by an elongate member 314. Two wires 316a, b and 316c,d are disposed in each lumen and extend out the distal end of elongate tubular members 312a, b, respectively. Actuating members 318a, b may be connected to the proximal ends of wires 316a-d such that movement of actuation members 318a, b in a distal direction moves wires 316a-d distally, extending wires 316a-d out of the distal ends of elongate tubular members 312a, b. Elongate member 314 has a vertical extension 315 that extends in a distal direction from elongate member 314. Vertical extension 315 may have a slot at the distal tip that is adapted to releasably hold a suture.

Figure 12B:
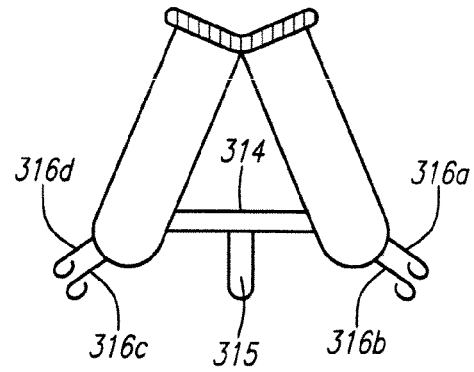
FIG. 12B is an anterior view of the embodiment of FIG. 12A in an expanded position.

FIG. 12B is an anterior view of the embodiment of the invention drawn in FIG. 12A. The device is drawn in its expanded position. The wires 316a-d extending from the tips of the tool are relatively stiff. The wires 316a-d extend away from the cylinders 312a, b of the tool as the wires 316a-d are advanced down the cylinders 312a, b. The tips of wires 316a-d are bent to grasp sutures or other flexible fixation members. The tool is used to form bands with materials that do not have sufficient stiffness to work in the previously described tools.

Figure 12C:
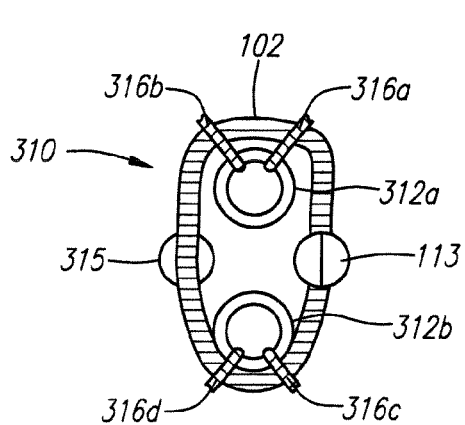
FIG. 12C is a view of the distal end of the embodiment in FIG. 12B showing a suture held in a band configuration.

FIG. 12C is a view of the distal end of the tool drawn in FIG. 12A, a suture, and a suture welding tool. Suture 102 is grasped and held in a band configuration by wires 316a-d, the slot in vertical extension 315, and the tip of a welding device 113. The device 310 is drawn in its contracted position.

Figure 12D:
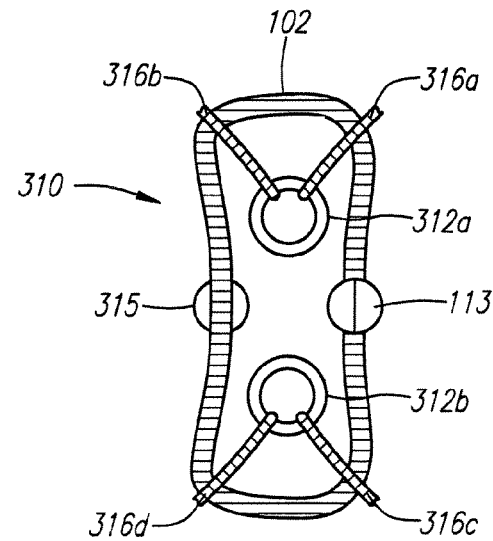
FIG. 12D is a view of the distal end of the embodiment in FIG. 12C holding the suture in an expanded configuration.

FIG. 12D is a view of the distal end of the tool drawn in FIG. 12C, a suture, and a suture welding tool. The device 310 is drawn in its expanded position. The device 310 and the welding tool can release the suture after the suture band is placed over the anchors, tightened, and welded or otherwise fastened. The slot in the vertical extension 315, located approximately opposite the tip 113 of the welding tool helps keep the waist of the suture band narrow.

Although the foregoing invention has, for the purposes of clarity and understanding, been described in some detail by way of illustration and example, it will be obvious that certain changes and modifications may be practiced which sill still fall within the scope of the appended claims.

What is claimed is:

1. A method for stabilizing a spinal segment comprising a first and second vertebrae and disc space therebetween comprising the steps of:

attaching first and second anchors to the first vertebra and third and fourth anchors to the second vertebra, each of said anchors comprising a shaft and an enlarged head;

positioning a first suture in a looped configuration to form a first suture loop around said shaft of said first anchor and said shaft of said third or fourth anchors, said first suture loop having overlapping first and second ends;

applying tension to said first and second ends of said first suture to tighten said first suture loop around said first anchor and one of said third and forth anchors;

welding said overlapping first and second ends of said first suture together to form a first band connecting said first anchor and said third or forth anchor;

positioning a second suture in a looped configuration to form a second suture loop around said shaft of said second anchor and said shaft of said third or fourth anchors, said second suture loop having overlapping first and second ends;

applying tension to said first and second ends of said second suture to tighten said second suture loop around said second anchor and one of said third and forth anchors;

welding said overlapping first and second ends of said second suture together to form a second band connecting said second anchor and said third or forth anchor;

wherein said positioning said first suture comprises advancing a banding tool adjacent to said first anchor and said third or fourth anchors, said banding tool holding said first suture in a looped configuration to form a first suture loop wherein said suture loop extends from a distal end of said banding tool and said first and second ends of said first suture overlap and extend from a proximal end of said banding tool.

2. The method of claim 1, wherein said positioning said second suture comprises advancing a banding tool adjacent to said second anchor and said third or fourth anchors, said banding tool holding said second suture in a looped configuration to form a second suture loop wherein said second suture loop extends from a distal end of said banding tool and said first and second ends of said second suture overlap and extend from a proximal end of said banding tool.

3. The method of claim 1, wherein said banding tool comprises an elongate tubular member having proximal and distal ends, a lumen therebetween, and a sidewall and wherein the distal end of the sidewall has at least one recess configured to hold said first suture in a looped configuration.

4. The method of claim 1, wherein said banding tool is releasably attached to a welding tool having first and second opposing jaws that define a gap therebetween, the jaws being operable between and open and a closed position, and a heating element in the distal region such that said overlapping portion of said first and second ends of said first suture is positioned between the gap.

5. The method of claim 1, wherein said positioning said first suture comprises advancing a banding tool adjacent to said first anchor and said third or fourth anchors, said banding tool holding said first suture in a looped configuration to form a first suture loop and said second suture in a looped configuration to form a second suture loop; and wherein positioning said second suture comprises moving said banding tool adjacent to said second anchor and said third or fourth anchors.

6. The method of claim 1, wherein applying tension across said first and second ends of said first suture further comprises tightening of the first suture loop such that the first anchor and the third or forth anchor are brought closer together and compression is applied to the disk space between the first and second vertebra.

7. The method of claim 1, wherein applying tension across said first and second ends of said second suture further comprises tightening the second suture loop such that the second anchor and the third or forth anchor are brought closer together and compression is applied to the disk space between the first and second vertebra.

8. A method for stabilizing spinal segment comprising first and second adjacent vertebrae comprising:

attaching first and second anchors to said first and second vertebra, each of said anchors having a shaft and an enlarged head;

advancing a suture banding tool adjacent to said first and second anchors, said suture banding tool comprising:
 a welding tool having first and second opposing jaws, that define a gap therebetween adapted to receive at least one suture portion and a heating element,
 a holding device releasably mounted on said welding tool, said holding device having at least one recess adapted to hold at least one suture portion in a looped configuration, and
 at least a first suture having first and second ends and a first looped portion therebetween, said at least first suture positioned in said holding device;

placing said first looped portion around said first and second anchors;

applying tension to said first and second ends of said first looped portion to tighten said first looped portion around said first and second anchors;

welding said first looped portion;

cutting said first and second ends from said first looped portion; and withdrawing said suture banding tool.

9. The method of claim 8, further comprising:

attaching third and forth anchors to said first and second vertebrae, each of said anchors having a shaft and an enlarged head;

positioning said suture banding tool adjacent to said third and fourth anchors, wherein said suture banding tool further comprises a second suture having first and second ends and a second looped portion therebetween, said second suture positioned in said holding device;

placing said second looped portion around said third and forth anchors;

applying tension to said second looped portion to tighten said second looped portion around said third and forth anchors;

welding said second looped portion; and cutting said first and second ends from said second looped portion.

10. The method of claim 8, wherein applying tension across said first looped portion further comprises tightening the first looped portion such that the first and second anchors are brought closer together and compression is applied to the disk space between the first and second vertebra.

11. The method of claim 8, wherein applying tension across said second looped portion further comprises tightening the second looped portion such that the third and fourth anchors are brought closer together and compression is applied to the disk space between the first and second vertebra.

* * * * *